US008362201B2

(12) United States Patent
King et al.

(10) Patent No.: US 8,362,201 B2
(45) Date of Patent: *Jan. 29, 2013

(54) INSECTICIDAL COMPOUNDS AND METHODS FOR SELECTION THEREOF

(75) Inventors: Glenn F. King, Chapel Hill (AU); Brianna Sollod McFarland, Windsor, CO (US)

(73) Assignee: University of Connecticut, Farmington, CT (US)

( * ) Notice: Subject to any disclaimer, the term of this patent is extended or adjusted under 35 U.S.C. 154(b) by 21 days.

This patent is subject to a terminal disclaimer.

(21) Appl. No.: 13/013,348

(22) Filed: Jan. 25, 2011

(65) Prior Publication Data

US 2011/0239331 A1 Sep. 29, 2011

Related U.S. Application Data

(60) Division of application No. 11/901,934, filed on Sep. 19, 2007, now Pat. No. 7,951,929, which is a division of application No. 10/655,751, filed on Sep. 5, 2003, now Pat. No. 7,279,547, which is a continuation-in-part of application No. 10/436,324, (Continued)

(51) Int. Cl.

| | |
|---|---|
| ***A01N 37/18*** | (2006.01) |
| ***C07K 14/00*** | (2006.01) |
| ***A01P 7/04*** | (2006.01) |
| ***G01N 33/566*** | (2006.01) |

(52) U.S. Cl. ..................... 530/300; 435/320.1; 435/348; 435/410; 435/69.1; 435/7.21; 514/4.5; 436/501

(58) Field of Classification Search ........................ None
See application file for complete search history.

(56) References Cited

U.S. PATENT DOCUMENTS

| | | | |
|---|---|---|---|
| 4,889,918 | A | 12/1989 | Krieg et al. |
| 5,338,544 | A | 8/1994 | Donovan |
| 5,382,429 | A | 1/1995 | Donovan et al. |
| 5,457,178 | A | 10/1995 | Jackson et al. |
| 5,578,702 | A | 11/1996 | Adang |
| 5,639,454 | A | 6/1997 | Thiem |
| 5,695,959 | A | 12/1997 | Jackson et al. |
| 5,731,194 | A | 3/1998 | Kalman et al. |
| 5,756,459 | A | 5/1998 | Jackson et al. |
| 5,759,809 | A | 6/1998 | Iatrou |
| 5,824,878 | A | 10/1998 | Ohba et al. |
| 5,942,664 | A | 8/1999 | Baum et al. |
| 5,959,182 | A | 9/1999 | Atkinson et al. |
| 5,962,264 | A | 10/1999 | Donova et al. |
| 5,962,765 | A | 10/1999 | St. Leger et al. |

(Continued)

FOREIGN PATENT DOCUMENTS

| | | |
|---|---|---|
| WO | 93/15108 | 8/1993 |
| WO | 99/58705 | 11/1999 |

OTHER PUBLICATIONS

Attwood, "The babel of bioinformatics", Science vol. 290, No. 5491 (2000), pp. 471-473.

(Continued)

*Primary Examiner* — Mary E Mosher
*Assistant Examiner* — Stuart W Snyder
(74) *Attorney, Agent, or Firm* — Honigman Miller Schwartz and Cohn LLP; Thomas A. Wootton; Jonathan P. O'Brien

(57) ABSTRACT

A series of potent and highly specific insecticidal toxins characterized by an amino acid sequences SEQ ID NO: 2-35.

5 Claims, 7 Drawing Sheets

Related U.S. Application Data filed on May 12, 2003, now Pat. No. 7,173,106, which is a division of application No. 09/780,874, filed on Feb. 9, 2001, now Pat. No. 6,583,264.

(60) Provisional application No. 60/181,532, filed on Feb. 10, 2000.

(56) References Cited

U.S. PATENT DOCUMENTS

| | | | | |
|---|---|---|---|---|
| 6,583,264 | B2 | 6/2003 | King et al. | |
| 7,173,106 | B2 * | 2/2007 | King et al. | 530/300 |
| 7,279,547 | B2 * | 10/2007 | King et al. | 530/300 |

OTHER PUBLICATIONS

Baker et al. "Protein structure predication and structural genomics", Science vol. 294, No. 5540 (2001), pp. 93-96.

Black et al. Commercialization of baculoviral insecticides, The Baculoviruses (Edited by Lois K. Miller), Chapter 13, (1997), pp. 341-387.

Burgess et al. Possible dissociation of the heparin-binding and mitogenic activities of heparin binding growth factor-1 from its receptor-binding activities by site directed mutagenesis of a single lysine residue, Journal of Cell Biology. vol. 111, (1990), pp. 2129-2138.

Cory et al. "Field Trial of a Genetically Improved Baculovirus Insecticide", Letters to Nature. vol. 370, (Jul. 14, 1994), pp. 138-140.

Estruch et al. "Transgenic Plants: An Emerging Approach to Pest Control", Nature Biotechnology, vol. 15, (Feb. 15, 1997), pp. 137-141.

Fletcher, "The Structure of a Novel Insecticidal Neurotoxin, co-atracotoxin-HV1 From the Venom of an Australian Funnel Web Spider", Nature Strutural Biology, vol. 4, (Jul. 1997), No. 7, pp. 559-566.

Genbank, Accession No. G29522, Ceres Incorporated, EP 1033405, Sep. 2000 (Jun. 9, 2000).

Grolleau, "Electrophysiological Analysis of the Neurotoxic Action of a Funnel-Web Spider Toxin, d-Atracotoxin-HV1a, On Insect Voltagegated Na+ Channels", J. Exp. Bio. vol. 204, (2001), pp. 711-721.

Lazar et al. "Transforming growth factor alpha: mutations of aspartic acid 47 and leucine 48 results in different biological activities", Molecular and Cellular Biology. vol. 8, No. 3 (1988), pp. 1247-1252.

N_Genseq_1101; Accession No. AAQ13318; patent No. JP03168087-A; Assignee: Kagaku Oyobi Kessi, Aug. 19, 1991.

Ngo et al. in The Protein Folding Problem and Tertiary Structure Prediction, 1994, Edited by Merz et al., (ed.), Birkhauser, Boston, MA, pp. 433 and 492-495.

PCT International Search Report dated Jan. 17, 2006.

Prikhod'ko et al. "Effects of Simultaneous Express of Two Sodium Channel Toxin Genes on the Properties of Baculoviruses as Biopesticides", Biological Control 12, (1998), pp. 66-78.

Riffkin et al. "A single amino-acid change between the antigenically different extracellular serine proteases V2 and B2 from Dichelobacter nodosus", Gene. vol. 167 (1995), pp. 279-283.

Riley et al., Cloning, Expression, and Spectroscopic Studies of the Jun Leucine Zipper Domain, FEBS, Eur. J. Biochem. vol. 219, (1994) pp. 877-886.

Scott et al. "The Pendred syndrome gene encodes a a chloride-iodide transport protein" Nature Genetics. vol. 21, (Apr. 1999), pp. 440-443.

Stemmer, "DNA Shuffling By Random Fragmentation and Reassembly: In Vitro Recombination for Molecular Evolution", Genetics, Proc. Natl. Acad. Sci. USA vol. 91, (Oct. 1994) pp. 10747-10751.

Stemmer, "Rapid Evolution of a Protein in Vitro by DNA Shuffling", Letters to Nature, vol. 370, (Aug. 4, 1994), pp. 389-391.

Wang et al. "Discovery and Structure of a Potent and Highly Specific Blocker of Insect Calcium Channels", J. Biol. Chem.; 2001.

Wang et al. "Structure-Function Studies of co-atracotoxin, A Potent Antagonist of Insect Voltage-Gated Calcium Channels", FEBS, Eur. J. Biochem. vol. 264, (1999), pp. 488-494.

Zhang et al. "Directed Evolution of a Fucosidase From A Galactosidase by DNA Shuffling and Screening", Evolution, Proc. Natl. Acad. Sci. USA, vol. 94, (Apr. 1997), pp. 4504-4509.

* cited by examiner

SEQUENCE LISTING

```
<160> NUMBER OF SEQ ID NOS: 36

<210> SEQ ID NO 1
<211> LENGTH: 45
<212> TYPE: PRT
<213> ORGANISM: Hadronyche versuta

<400> SEQUENCE: 1

Leu Leu Ala Cys Leu Phe Gly Asn Gly Arg Cys Ser Ser Asn Arg Asp
1               5                   10                  15

Cys Cys Glu Leu Thr Pro Val Cys Lys Arg Gly Ser Cys Val Ser Ser
            20                  25                  30

Gly Pro Gly Leu Val Gly Gly Ile Leu Gly Gly Ile Leu
        35                  40                  45


<210> SEQ ID NO 2
<211> LENGTH: 98
<212> TYPE: PRT
<213> ORGANISM: Hadronyche versuta

<400> SEQUENCE: 2

Met Lys Phe Ser Lys Leu Ser Leu Thr Leu Ala Leu Ile Leu Thr Gln
1               5                   10                  15

Ala Ile Phe Val Leu Cys Gly Lys Ile Asn Glu Asp Phe Met Lys Asn
            20                  25                  30

Asp Leu Glu Ser Gln Ala Leu His Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Val Cys Ser Ser Asp Lys Asp Cys Cys Gly Met Thr Pro Ser Cys
```

```
65                  70                  75                  80

Thr Met Gly Leu Cys Val Pro Ser Val Gly Gly Leu Val Gly Gly Ile
                85                  90                  95

Leu Gly


<210> SEQ ID NO 3
<211> LENGTH: 98
<212> TYPE: PRT
<213> ORGANISM: Atrax robustus

<400> SEQUENCE: 3

Met Lys Phe Ser Lys Leu Ser Leu Thr Leu Ala Leu Ile Leu Thr Gln
1               5                   10                  15

Ala Leu Phe Val Leu Cys Gly Lys Ile Asn Glu Asp Phe Met Lys Asn
            20                  25                  30

Gly Leu Glu Ser Gln Thr Leu His Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Val Cys Ser Ser Asp Arg Asp Cys Cys Gly Met Thr Pro Ser Cys
65                  70                  75                  80

Thr Met Gly Leu Cys Val Pro Asn Val Gly Gly Leu Val Gly Gly Ile
                85                  90                  95

Leu Gly


<210> SEQ ID NO 4
<211> LENGTH: 98
<212> TYPE: PRT
<213> ORGANISM: Hadronyche versuta

<400> SEQUENCE: 4

Met Lys Phe Ser Lys Leu Ser Leu Thr Leu Ala Leu Ile Leu Thr Gln
1               5                   10                  15

Ala Ile Phe Val Leu Cys Gly Lys Ile Asn Glu Asp Phe Met Lys Asn
            20                  25                  30

Asp Leu Glu Ser Gln Ala Leu Arg Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Val Cys Ser Ser Asp Lys Asp Cys Cys Gly Met Thr Pro Ser Cys
65                  70                  75                  80

Thr Met Gly Leu Cys Val Pro Ser Val Gly Gly Leu Val Gly Gly Ile
                85                  90                  95

Leu Gly


<210> SEQ ID NO 5
<211> LENGTH: 98
<212> TYPE: PRT
<213> ORGANISM: Hadronyche versuta

<400> SEQUENCE: 5

Met Lys Phe Ser Lys Leu Ser Leu Thr Leu Ala Leu Ile Leu Thr Gln
1               5                   10                  15

Ala Ile Phe Val Leu Cys Gly Lys Ile Asn Glu Asp Phe Met Lys Asn
            20                  25                  30

Asp Leu Glu Ser His Ala Leu His Asp Glu Ile Arg Lys Pro Ile Asn
        35                  40                  45
```

-continued

```
Ser Glu Asn Pro Asp Thr Glu Arg Leu Leu Asp Cys Leu Leu Asp Asn
    50                  55                  60

Arg Val Cys Ser Ser Asp Lys Asp Cys Cys Gly Met Thr Pro Ser Cys
65                  70                  75                  80

Thr Met Gly Leu Cys Val Pro Ser Val Gly Gly Leu Val Gly Gly Ile
                85                  90                  95

Leu Gly


<210> SEQ ID NO 6
<211> LENGTH: 98
<212> TYPE: PRT
<213> ORGANISM: Hadronyche versuta

<400> SEQUENCE: 6

Met Lys Phe Ser Lys Leu Ser Leu Thr Leu Ala Leu Ile Leu Thr Gln
1               5                   10                  15

Ala Leu Phe Val Leu Cys Gly Lys Ile Asn Glu Asp Phe Met Lys Asn
            20                  25                  30

Gly Leu Glu Ser Gln Ala Leu His Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Val Cys Ser Ser Asp Lys Asp Cys Cys Gly Met Thr Pro Ser Cys
65                  70                  75                  80

Thr Met Gly Leu Cys Val Pro Ser Val Gly Gly Leu Val Gly Gly Ile
                85                  90                  95

Leu Gly


<210> SEQ ID NO 7
<211> LENGTH: 98
<212> TYPE: PRT
<213> ORGANISM: Hadronyche versuta

<400> SEQUENCE: 7

Met Lys Phe Ser Lys Leu Ser Leu Thr Leu Ala Leu Ile Leu Thr Gln
1               5                   10                  15

Val Ile Phe Val Leu Cys Gly Lys Ile Asn Glu Asp Phe Met Lys Asn
            20                  25                  30

Gly Leu Glu Ser Gln Ala Leu His Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Val Cys Ser Ser Asp Lys Asp Cys Cys Gly Met Thr Pro Ser Cys
65                  70                  75                  80

Thr Met Gly Leu Cys Val Pro Ser Val Gly Gly Leu Val Gly Gly Ile
                85                  90                  95

Leu Gly


<210> SEQ ID NO 8
<211> LENGTH: 93
<212> TYPE: PRT
<213> ORGANISM: Hadronyche versuta

<400> SEQUENCE: 8

Met Lys Phe Ser Lys Leu Ser Leu Thr Leu Ala Leu Ile Leu Thr Gln
1               5                   10                  15

Ala Leu Phe Val Leu Cys Asp Phe Met Lys Asn Gly Leu Glu Ser Gln
            20                  25                  30
```

-continued

```
Ala Leu His Asp Glu Ile Arg Lys Ser Ile Asp Ser Glu Asn Pro Asp
        35                  40                  45

Thr Glu Arg Leu Leu Asp Cys Leu Leu Asp Asn Arg Val Cys Ser Ser
    50                  55                  60

Asp Lys Asp Cys Cys Gly Met Thr Pro Ser Cys Thr Met Gly Leu Cys
65                  70                  75                  80

Val Pro Ser Val Gly Gly Leu Val Gly Gly Ile Leu Gly
                85                  90


<210> SEQ ID NO 9
<211> LENGTH: 98
<212> TYPE: PRT
<213> ORGANISM: Atrax robustus

<400> SEQUENCE: 9

Met Lys Phe Ser Lys Leu Ser Leu Thr Leu Ala Leu Ile Leu Thr Gln
1               5                   10                  15

Val Leu Phe Val Leu Cys Gly Lys Ile Asn Glu Asp Phe Met Lys His
            20                  25                  30

Gly Leu Glu Ser Gln Ala Leu His Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Val Cys Ser Ser Asp Lys Asp Cys Cys Gly Met Thr Pro Ser Cys
65                  70                  75                  80

Thr Met Gly Leu Cys Val Pro Ser Val Gly Gly Leu Val Gly Gly Ile
                85                  90                  95

Leu Gly


<210> SEQ ID NO 10
<211> LENGTH: 98
<212> TYPE: PRT
<213> ORGANISM: Hadronyche versuta

<400> SEQUENCE: 10

Met Lys Phe Ser Lys Leu Ser Leu Thr Leu Ala Leu Ile Leu Thr Gln
1               5                   10                  15

Ala Ile Phe Val Leu Cys Gly Lys Ile Asn Glu Asp Phe Met Lys Asn
            20                  25                  30

Asp Leu Glu Ser Gln Ala Leu His Asp Glu Ile Arg Lys Pro Ile Asn
        35                  40                  45

Ser Glu Asn Pro Asp Thr Glu Arg Leu Leu Asp Cys Leu Leu Asp Asn
    50                  55                  60

Arg Val Cys Ser Ser Asp Lys Asp Cys Cys Gly Met Thr Pro Ser Cys
65                  70                  75                  80

Thr Met Gly Leu Cys Val Pro Ser Val Gly Gly Leu Val Gly Gly Ile
                85                  90                  95

Leu Gly


<210> SEQ ID NO 11
<211> LENGTH: 98
<212> TYPE: PRT
<213> ORGANISM: Hadronyche versuta

<400> SEQUENCE: 11

Met Lys Phe Ser Lys Leu Ser Leu Thr Leu Ala Leu Ile Leu Thr Gln
1               5                   10                  15
```

-continued

```
Ala Leu Phe Val Leu Cys Gly Lys Ile Asn Glu Asp Phe Met Lys Asn
            20                  25                  30

Gly Leu Glu Ser Gln Ala Leu His Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Val Cys Ser Ser Asp Arg Asp Cys Cys Gly Met Thr Pro Ser Cys
65                  70                  75                  80

Thr Met Gly Leu Cys Val Pro Asn Val Gly Gly Leu Val Gly Asp Ile
                85                  90                  95

Leu Gly


<210> SEQ ID NO 12
<211> LENGTH: 97
<212> TYPE: PRT
<213> ORGANISM: Hadronyche versuta

<400> SEQUENCE: 12

Met Lys Phe Ser Lys Leu Ser Leu Thr Leu Ala Leu Ile Leu Thr Gln
1               5                   10                  15

Val Leu Phe Val Leu Cys Gly Lys Ile Glu Asp Phe Met Lys Asn Gly
            20                  25                  30

Leu Glu Ser Gln Ala Leu His Asp Glu Ile Arg Lys Pro Ile Asp Ser
        35                  40                  45

Glu Asn Pro Asp Thr Glu Arg Leu Leu Asp Cys Leu Leu Asp Asn Arg
    50                  55                  60

Val Cys Ser Ser Asp Lys Asp Cys Cys Gly Met Thr Pro Ser Cys Thr
65                  70                  75                  80

Met Gly Leu Cys Val Pro Asn Val Gly Gly Leu Val Gly Gly Ile Leu
                85                  90                  95

Gly


<210> SEQ ID NO 13
<211> LENGTH: 93
<212> TYPE: PRT
<213> ORGANISM: Hadronyche versuta

<400> SEQUENCE: 13

Met Lys Phe Ser Lys Leu Ser Leu Thr Leu Ala Leu Ile Leu Thr Gln
1               5                   10                  15

Ala Leu Phe Val Leu Cys Asp Phe Met Lys Asn Gly Leu Glu Ser Gln
            20                  25                  30

Ala Leu His Asp Glu Ile Arg Lys Pro Ile Asp Ser Glu Asn Pro Asp
        35                  40                  45

Thr Glu Arg Leu Leu Asp Cys Leu Leu Asp Asn Arg Val Cys Ser Ser
    50                  55                  60

Asp Lys Asp Cys Cys Gly Met Thr Pro Ser Cys Thr Met Gly Leu Cys
65                  70                  75                  80

Val Pro Asn Val Gly Gly Leu Val Gly Gly Ile Leu Gly
                85                  90


<210> SEQ ID NO 14
<211> LENGTH: 98
<212> TYPE: PRT
<213> ORGANISM: Hadronyche versuta

<400> SEQUENCE: 14

Met Lys Phe Ser Lys Leu Ser Leu Thr Leu Ala Leu Ile Leu Thr Gln
```

-continued

```
1               5                   10                  15

Ala Leu Phe Val Leu Cys Gly Lys Ile Asn Glu Asp Phe Met Lys Asn
            20                  25                  30

Gly Leu Glu Ser Gln Ala Leu His Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Ile Cys Ser Ser Asp Lys Asp Cys Cys Gly Met Thr Pro Ser Cys
65                  70                  75                  80

Thr Met Gly Leu Cys Val Pro Asn Val Gly Gly Leu Val Gly Gly Ile
                85                  90                  95

Leu Gly
```

<210> SEQ ID NO 15
<211> LENGTH: 98
<212> TYPE: PRT
<213> ORGANISM: Hadronyche versuta

<400> SEQUENCE: 15

```
Met Lys Phe Ser Lys Leu Ser Leu Thr Leu Ala Leu Ile Leu Thr Gln
1               5                   10                  15

Ala Leu Phe Val Leu Cys Gly Lys Ile Asn Glu Asp Phe Met Lys Asn
            20                  25                  30

Gly Leu Glu Ser Gln Ala Leu His Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Val Cys Ser Ser Asp Lys Asp Cys Cys Gly Met Thr Pro Ser Cys
65                  70                  75                  80

Thr Met Gly Leu Cys Val Pro Asn Val Gly Gly Leu Val Gly Gly Ile
                85                  90                  95

Leu Gly
```

<210> SEQ ID NO 16
<211> LENGTH: 98
<212> TYPE: PRT
<213> ORGANISM: Hadronyche versuta

<400> SEQUENCE: 16

```
Met Lys Phe Ser Lys Leu Ser Leu Thr Leu Ala Leu Ile Leu Thr Gln
1               5                   10                  15

Ala Ile Phe Val Leu Cys Gly Lys Ile Asn Glu Asp Phe Met Lys Asn
            20                  25                  30

Asp Leu Glu Ser Gln Ala Leu His Asp Glu Ile Arg Lys Pro Ile Asn
        35                  40                  45

Ser Glu Asn Pro Asp Thr Glu Arg Leu Leu Asp Cys Leu Leu Asp Ser
    50                  55                  60

Arg Val Cys Ser Ser Asp Lys Asp Cys Cys Gly Met Thr Pro Ser Cys
65                  70                  75                  80

Thr Met Gly Leu Cys Val Pro Ser Val Gly Gly Leu Val Gly Gly Ile
                85                  90                  95

Leu Gly
```

<210> SEQ ID NO 17
<211> LENGTH: 96
<212> TYPE: PRT
<213> ORGANISM: Atrax robustus

<400> SEQUENCE: 17

```
Met Lys Phe Ser Lys Leu Ser Ile Thr Leu Ala Val Ile Leu Thr Gln
1               5                   10                  15

Ala Val Phe Val Phe Cys Gly Met Thr Asn Glu Asp Phe Met Glu Lys
            20                  25                  30

Gly Leu Glu Ser Asn Glu Leu Pro Asp Ala Ile Lys Lys Pro Val Asn
        35                  40                  45

Ser Gly Lys Pro Asp Thr Lys Arg Leu Leu Asp Cys Val Leu Ser Arg
    50                  55                  60

Met Cys Phe Ser Asn Ala Asn Cys Cys Gly Leu Thr Pro Pro Cys Lys
65                  70                  75                  80

Met Gly Leu Cys Val Pro Asn Val Gly Gly Leu Leu Gly Gly Ile Leu
                85                  90                  95
```

<210> SEQ ID NO 18
<211> LENGTH: 96
<212> TYPE: PRT
<213> ORGANISM: Atrax robustus

<400> SEQUENCE: 18

```
Met Lys Phe Ser Lys Leu Ser Ile Thr Leu Ala Val Ile Leu Thr Gln
1               5                   10                  15

Ala Val Phe Val Phe Cys Gly Met Thr Asn Glu Asp Phe Met Glu Lys
            20                  25                  30

Gly Leu Glu Ser Asn Glu Leu His Asp Ala Ile Lys Lys Pro Val Asn
        35                  40                  45

Ser Gly Lys Pro Asp Thr Glu Arg Leu Leu Asp Cys Val Leu Ser Arg
    50                  55                  60

Met Cys Ser Ser Asp Ala Asn Cys Cys Gly Leu Thr Pro Thr Cys Lys
65                  70                  75                  80

Met Gly Leu Cys Val Pro Asn Val Gly Gly Leu Leu Gly Gly Ile Leu
                85                  90                  95
```

<210> SEQ ID NO 19
<211> LENGTH: 101
<212> TYPE: PRT
<213> ORGANISM: Hadronyche versuta

<400> SEQUENCE: 19

```
Met Lys Phe Ser Lys Leu Ser Leu Thr Leu Ala Leu Ile Leu Thr Gln
1               5                   10                  15

Ala Leu Phe Val Leu Cys Gly Lys Ile Asn Glu Asp Phe Met Glu His
            20                  25                  30

Gly Leu Glu Ser His Ala Leu His Asp Glu Ile Arg Lys Pro Ile Asp
        35                  40                  45

Thr Glu Lys Ala Asp Ala Glu Arg Leu Val Asp Cys Val Val Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Arg Gly Leu Val Gly Gly Leu
                85                  90                  95

Leu Gly Arg Ala Leu
            100
```

<210> SEQ ID NO 20
<211> LENGTH: 101
<212> TYPE: PRT

<213> ORGANISM: Hadronyche versuta

<400> SEQUENCE: 20

```
Met Lys Phe Ser Lys Leu Ser Leu Thr Leu Ala Leu Ile Leu Thr Gln
1               5                   10                  15

Ala Leu Phe Val Leu Cys Met Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Glu Lys Ala Asp Ala Glu Arg Leu Val Asp Cys Val Val Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Leu Val Gly Gly Leu
                85                  90                  95

Leu Gly Arg Ala Leu
            100
```

<210> SEQ ID NO 21
<211> LENGTH: 101
<212> TYPE: PRT
<213> ORGANISM: Hadronyche versuta

<400> SEQUENCE: 21

```
Met Lys Phe Ser Lys Leu Ser Leu Thr Phe Ala Leu Ile Leu Thr Gln
1               5                   10                  15

Ala Leu Phe Val Leu Cys Gly Lys Ile Asn Glu Asp Phe Met Asp Asn
            20                  25                  30

Gly Leu Glu Ser His Ala Leu His Asp Glu Ile Arg Lys Pro Ile His
        35                  40                  45

Thr Glu Lys Ala Asp Ala Glu Arg Leu Val Asp Cys Val Leu Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Leu Val Gly Gly Leu
                85                  90                  95

Leu Gly Arg Ala Leu
            100
```

<210> SEQ ID NO 22
<211> LENGTH: 101
<212> TYPE: PRT
<213> ORGANISM: Hadronyche infensa

<400> SEQUENCE: 22

```
Met Lys Phe Ser Lys Leu Ser Leu Thr Leu Ala Leu Ile Leu Thr Gln
1               5                   10                  15

Ala Leu Phe Val Leu Cys Gly Lys Ile Asn Glu Asp Phe Met Glu His
            20                  25                  30

Gly Leu Glu Ser His Ala Leu His Asp Glu Ile Arg Lys Pro Ile Asp
        35                  40                  45

Thr Glu Lys Ala Asp Ala Glu Arg Leu Val Asp Cys Val Val Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Leu Val Gly Gly Leu
                85                  90                  95
```

```
Leu Gly Arg Ala Leu
            100


<210> SEQ ID NO 23
<211> LENGTH: 101
<212> TYPE: PRT
<213> ORGANISM: Hadronyche infensa

<400> SEQUENCE: 23

Met Lys Phe Ser Lys Leu Ser Val Thr Leu Ala Leu Ile Leu Thr Gln
1               5                   10                  15

Thr Leu Leu Val Leu Cys Gly Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Asp Lys Ala Tyr Ala Glu Arg Val Leu Asp Cys Val Val Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Leu Val Gly Gly Leu
                85                  90                  95

Leu Gly Arg Ala Leu
            100


<210> SEQ ID NO 24
<211> LENGTH: 101
<212> TYPE: PRT
<213> ORGANISM: Hadronyche versuta

<400> SEQUENCE: 24

Met Lys Phe Ser Lys Leu Ser Leu Thr Leu Ala Leu Ile Leu Thr Gln
1               5                   10                  15

Ala Leu Phe Val Leu Cys Gly Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Glu Lys Ala Asp Ala Glu Arg Leu Val Asp Cys Val Val Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Leu Val Gly Gly Leu
                85                  90                  95

Leu Gly Arg Ala Leu
            100


<210> SEQ ID NO 25
<211> LENGTH: 101
<212> TYPE: PRT
<213> ORGANISM: Hadronyche versuta

<400> SEQUENCE: 25

Met Lys Phe Ser Lys Leu Ser Leu Thr Leu Ala Leu Ile Leu Thr Gln
1               5                   10                  15

Ala Leu Phe Val Leu Cys Gly Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Glu Lys Ala Asp Ala Glu Arg Val Leu Asp Cys Val Val Asn Thr
    50                  55                  60
```

```
Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Leu Val Gly Gly Leu
                85                  90                  95

Leu Gly Arg Ala Leu
            100


<210> SEQ ID NO 26
<211> LENGTH: 100
<212> TYPE: PRT
<213> ORGANISM: Hadronyche versuta

<400> SEQUENCE: 26

Met Lys Phe Ser Lys Leu Ser Leu Thr Leu Ala Leu Ile Leu Thr Gln
1               5                   10                  15

Ala Leu Phe Val Leu Cys Gly Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Glu Lys Ala Asp Ala Glu Arg Leu Val Asp Cys Val Val Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Leu Val Gly Gly Leu Leu
                85                  90                  95

Gly Arg Ala Leu
            100


<210> SEQ ID NO 27
<211> LENGTH: 97
<212> TYPE: PRT
<213> ORGANISM: Atrax robustus

<400> SEQUENCE: 27

Met Lys Phe Ser Lys Leu Ser Ile Thr Leu Ala Val Ile Leu Thr Gln
1               5                   10                  15

Ala Val Phe Val Phe Cys Gly Met Thr Asn Glu Asp Phe Met Glu Lys
            20                  25                  30

Gly Phe Lys Ser Asn Asp Leu Gln Tyr Ala Ile Lys Gln Pro Val Asn
        35                  40                  45

Ser Gly Lys Pro Asp Thr Glu Arg Leu Leu Asp Cys Val Leu Ser Arg
    50                  55                  60

Val Cys Ser Ser Asp Glu Asn Cys Cys Gly Leu Thr Pro Thr Cys Thr
65                  70                  75                  80

Met Gly Leu Cys Val Pro Asn Val Gly Gly Leu Leu Gly Gly Leu Leu
                85                  90                  95

Ser


<210> SEQ ID NO 28
<211> LENGTH: 97
<212> TYPE: PRT
<213> ORGANISM: Atrax robustus

<400> SEQUENCE: 28

Met Lys Phe Ser Lys Leu Ser Ile Thr Leu Val Val Ile Leu Thr Gln
1               5                   10                  15

Ala Val Phe Val Phe Cys Gly Met Thr Asn Glu Asp Phe Met Glu Lys
            20                  25                  30
```

-continued

Gly Phe Lys Ser Asn Asp Leu Gln Tyr Ala Ile Arg Gln Pro Val Asn
35 40 45

Ser Gly Lys Pro Asp Thr Glu Arg Leu Leu Asp Cys Val Leu Ser Arg
50 55 60

Val Cys Ser Ser Asp Glu Asn Cys Cys Gly Leu Thr Pro Thr Cys Thr
65 70 75 80

Met Gly Leu Cys Val Pro Asn Val Gly Gly Leu Leu Gly Gly Leu Leu
85 90 95

Ser

<210> SEQ ID NO 29
<211> LENGTH: 101
<212> TYPE: PRT
<213> ORGANISM: Hadronyche versuta

<400> SEQUENCE: 29

Met Lys Phe Ser Lys Leu Ser Leu Thr Leu Ala Leu Ile Leu Thr Gln
1 5 10 15

Ala Leu Leu Val Leu Cys Gly Lys Ile Asn Glu Asp Phe Met Glu Asn
20 25 30

Gly Leu Glu Ser His Ala Leu His Asp Glu Ile Arg Lys Pro Leu Asp
35 40 45

Thr Glu Asn Pro Asp Thr Glu Arg Gln Leu Asp Cys Val Leu Asn Thr
50 55 60

Leu Gly Cys Ser Ser Asp Lys Asp Cys Cys Gly Met Thr Pro Ser Cys
65 70 75 80

Thr Leu Gly Ile Cys Ala Pro Asn Val Gly Gly Leu Val Gly Gly Leu
85 90 95

Leu Gly Arg Ala Leu
100

<210> SEQ ID NO 30
<211> LENGTH: 101
<212> TYPE: PRT
<213> ORGANISM: Hadronyche versuta

<400> SEQUENCE: 30

Met Lys Phe Ser Lys Leu Ser Leu Thr Leu Ala Leu Ile Leu Thr Gln
1 5 10 15

Val Leu Leu Val Val Cys Gly Lys Ile Asn Glu Asp Phe Met Glu Asn
20 25 30

Gly Leu Glu Ser His Ala Leu His Asp Glu Ile Arg Lys Pro Ile Asp
35 40 45

Thr Glu Lys Ala Asp Ala Glu Arg Val Leu Asp Cys Val Val Asn Thr
50 55 60

Leu Gly Cys Ser Ser Asp Lys Asp Cys Cys Gly Met Thr Pro Ser Cys
65 70 75 80

Thr Leu Gly Ile Cys Ala Pro Ser Val Gly Gly Ile Val Gly Gly Leu
85 90 95

Leu Gly Arg Ala Leu
100

<210> SEQ ID NO 31
<211> LENGTH: 101
<212> TYPE: PRT
<213> ORGANISM: Hadronyche versuta

<400> SEQUENCE: 31

```
Met Lys Phe Ser Lys Leu Ser Leu Thr Leu Ala Leu Ile Leu Ala Gln
1               5                   10                  15

Ala Ile Phe Val Leu Cys Gly Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Glu Lys Ala Asp Ala Glu Arg Val Val Asp Cys Val Leu Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Leu Val Gly Gly Leu
                85                  90                  95

Leu Gly Arg Ala Leu
            100


<210> SEQ ID NO 32
<211> LENGTH: 101
<212> TYPE: PRT
<213> ORGANISM: Hadronyche versuta

<400> SEQUENCE: 32

Met Lys Phe Ser Lys Leu Ser Leu Thr Leu Ala Leu Ile Leu Thr Gln
1               5                   10                  15

Ala Leu Leu Val Val Cys Gly Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Glu Lys Ala Asp Ala Glu Arg Val Leu Asp Cys Val Val Asn Ile
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Ile Val Gly Gly Leu
                85                  90                  95

Leu Gly Arg Ala Leu
            100


<210> SEQ ID NO 33
<211> LENGTH: 101
<212> TYPE: PRT
<213> ORGANISM: Hadronyche versuta

<400> SEQUENCE: 33

Met Lys Phe Ser Lys Leu Ser Leu Thr Leu Ala Leu Ile Leu Thr Gln
1               5                   10                  15

Ala Leu Leu Val Val Cys Gly Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Glu Lys Ala Asp Ala Glu Arg Val Leu Asp Cys Val Val Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Ile Val Gly Gly Leu
                85                  90                  95

Leu Gly Arg Ala Leu
            100
```

-continued

```
<210> SEQ ID NO 34
<211> LENGTH: 101
<212> TYPE: PRT
<213> ORGANISM: Hadronyche infensa

<400> SEQUENCE: 34

Met Lys Phe Ser Lys Leu Ser Leu Thr Leu Ala Leu Ile Leu Thr Gln
1               5                   10                  15

Ala Leu Leu Val Val Cys Gly Lys Ile Asn Glu Asp Phe Met Glu Asn
            20                  25                  30

Gly Leu Glu Ser His Ala Leu His Asp Glu Ile Arg Lys Ser Ile Asp
        35                  40                  45

Thr Glu Lys Ala Asp Ala Glu Arg Val Leu Asp Cys Val Val Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Ile Val Gly Gly Leu
                85                  90                  95

Leu Gly Arg Ala Leu
            100


<210> SEQ ID NO 35
<211> LENGTH: 95
<212> TYPE: PRT
<213> ORGANISM: Hadronyche versuta

<400> SEQUENCE: 35

Met Lys Phe Ser Lys Leu Ser Leu Thr Phe Ala Leu Ile Leu Thr Gln
1               5                   10                  15

Thr Leu Leu Val Leu Cys Asp Phe Met Glu Asn Gly Leu Glu Ser His
            20                  25                  30

Ala Leu His Asp Glu Ile Arg Lys Pro Ile Asp Thr Glu Lys Ala Asp
        35                  40                  45

Ala Glu Arg Val Leu Asp Cys Val Val Asn Thr Leu Gly Cys Ser Ser
    50                  55                  60

Asp Lys Asp Cys Cys Gly Met Thr Pro Ser Cys Thr Leu Gly Ile Cys
65                  70                  75                  80

Ala Pro Ser Val Gly Gly Leu Val Gly Gly Leu Leu Gly Arg Ala
                85                  90                  95


<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 36

gggcaggttt tttttttttt tttt                                            24
```

INSECTICIDAL COMPOUNDS AND METHODS FOR SELECTION THEREOF

This application is a continuation application of U.S. patent application Ser. No. 11/901,934, filed Sep. 19, 2007, which is a divisional application of U.S. patent application Ser. No. 10/655,751 filed Sep. 5, 2003, which is a continuation in part of U.S. patent application Ser. No. 10/436,324, filed May 12, 2003, which is a divisional application of U.S. patent application Ser. No. 09/780,874, filed Feb. 9, 2011, which claims the benefit of U.S. Provisional Patent Application Ser. No. 60/181,532, filed Feb. 10, 2000, all of which are incorporated herein by reference in their entirety.

1. FIELD OF THE INVENTION

The present invention relates to biological compounds, and genes encoding biological compounds, for use as pesticides, as well as methods for obtaining such compounds.

2. BACKGROUND OF THE RELATED ART

Unfortunately, it has increasingly been seen over the past several decades that employment of conventional chemical insecticides often leads to undesirable environmental consequences. Such consequences include toxicity to non-target organisms such as birds and fish, and human health hazards. Furthermore, pesticide management in the United States and elsewhere in the world is becoming increasingly complicated due to the evolution of insect resistance to classical chemical pesticides. Despite over 10 billion dollars being spent each year to control phytophagus insects, global losses in the food supply due to insects is still estimated to be about 20 to 30 percent (See, Oerke, *Estimated crop losses due to pathogens, animal pests and weeds,* 72-78 in *Crop production and crop protection: Estimated losses in major food and cash crops* (Elsevier, Amsterdam 1994)). There remains, therefore, an urgent need to develop or obtain substances that can be used safely in the fight against insect pests.

Over the past several years, there have been proposed a number of "environmentally friendly" strategies to combat highly resistant insect pests such as certain species of cotton bollworm (e.g., *Helicoverpa zea*).

One recently introduced approach to insect management is the production of transgenic crops that express insecticidal toxins, such as engineered potato and cotton crops that express protein toxins from the soil bacterium *Bacillus thuringiensis* (Estruch, J. J. et al., *Transgenic plants: An emerging approach to pest control*, Nature Biotechnology 15, 137-141, 1997).

A variation of this strategy is the release of insect-specific viruses that have been genetically engineered to express insecticidal neurotoxins (Cory, J. S. et al., *Field trial of a genetically improved baculovirus insecticide*, Nature 370, 138-140, 1994). Baculoviruses, for example, are arthropod-specific viruses with no member of the baculovirus family known to infect either vertebrates or plants. The infectivity of some baculoviruses is restricted to a few closely related species within a single family of lepidopterous insects (moths and butterflies) (See, e.g., U.S. Pat. No. 5,639,454). Some baculoviruses, such as the beet armyworm nuclear polyhedrosis virus, target only a single species. As a result of their high degree of specificity, baculoviruses have long been envisaged as potential pest control agents and were first used as such in the 1970s. Their specificity means that baculoviral insecticides complement natural predators, rather than replacing them, as is the case with many chemical insecticides. However, to date, baculoviruses have met with only limited commercial success. Most naturally occurring baculoviruses take 4-7 days to kill their hosts, with some species taking considerably longer. During this time the insect continues to feed and cause crop damage, thus limiting the ability of baculoviral insecticides to compete with chemical agents.

This shortcoming has been addressed by engineering recombinant baculoviruses that express insect-specific neurotoxins. Expression of heterologous insect toxins not only reduces the time interval between virus application and insect death, but also reduces the mean feeding time (Prikhod'ko et al., *Effects of simultaneous expression of two sodium channel toxin genes on the properties of baculoviruses as biopesticides*, Biological Control 12, 66-78, 1998). Importantly, introduction of genes for insect-selective toxins does not alter the intrinsic infectivity of the baculovirus or its natural host range (Black et al., *Commercialization of baculoviral insecticides*, in *The Baculoviruses* (ed. Miller, L. K.) 341-387 (Plenum Press, New York, USA, 1997)).

New approaches to insect-pest management have stimulated interest in peptide toxins from the venoms of animals, particularly spiders and scorpions, that prey on insect species. Zlotkin et al., *An Excitatory and a Depressant Insect Toxin from Scorpion Venom both Affect Sodium Conductance and Possess a Common Binding Site*, Arch. Biochem. and Biophysics 240, 877-887, 1985), disclose two insect selective toxins from the venom of the scorpion *Leiurus quinqestriatus*, one of which induced fast excitatory contractive paralysis of fly larvae while the other induced slow depressant flaccid paralysis, with both affecting sodium conductance in the neurons. Likewise, Canadian patent 2,005,658 (issued: Jun. 19, 1990 to Zlotkin et al.) discloses an insecticidally effective protein referred to as "LqhP35" derived from the scorpion *Leiurus quinquestriatus hebraeus.*

A number of investigators have also recognized spider venoms as a possible source of insect-specific toxins for agricultural applications (See, Jackson et al., Ann. Rev. Neurosci. 12, 405-414 (1989)). For example, U.S. Pat. Nos. 4,855,405 (issued: Aug. 8, 1989 to Yoshioka et al.) and 4,918, 107 (issued: Apr. 17, 1990 to Nakajima et al.) both disclose glutamate-receptor inhibitors obtained from the venom of spiders as possible insecticidal agents. In U.S. Pat. Nos. 5,457,178 (issued: Oct. 10, 1995), 5,695,959 (issued: Dec. 9, 1997), and 5,756,459 (issued: May 26, 1998), Jackson et al., disclose a family of insecticidally effective proteins isolated from the venom of the spiders *Filistata hibernalis* (a common house spider) and *Phidippus audax* (a "jumping spider").

A particular group of spiders which has generated considerable investigative interest are the funnel-web spiders. WO 89/07608 (published: Aug. 24, 1989, Cherksey et al.) discloses low molecular weight factors isolated from American funnel-web spider venoms which reversibly bind to calcium channels. Adams et al., *Isolation and Biological Activity of Synaptic Toxins from the Venom of the Funnel Web Spider, Agelenopsis aperta*, in *Insect Neurochemistry and Neurophysiology*, Borkovec and Gelman (eds.) (Humana Press, New Jersey, 1986) teaches that multiple peptide toxins which antagonize synaptic transmission in insects have been isolated from the spider *Agelenopsis aperta*. In WO 93/15108, a class of peptide toxins known as the ω-atracotoxins are disclosed as being isolated from the Australian funnel-web spiders (Araneae:Hexathelidae:Atracinae) by screening the venom for anti-*Helicoverpa* ("anti-cotton bollworm") activity. Such toxins are disclosed to have a molecular weight of approximately 4000 amu, to be of 36-37 amino acids in length, and capable of forming three intrachain disulfide bridges. One of these compounds, designated ω-ACTX-Hv1 has been shown to selectively inhibit insect, as opposed to mammalian, voltage-gated calcium channel currents (Fletcher et al., *The structure of a novel insecticidal neurotoxin*, *ω-atracotoxin-Hv*1, *from the venom of an Australian funnel web spider*, Nature Struct. Biol. 4, 559-566 (1997)). Homologues of ω-ACTX-Hv1 have been isolated from the Blue Mountain funnel-web spider *Hadronyche versuta* (See, Wang et al., *Structure-function of* ω-*atrocotoxin, a potent antagonist of insect voltage-gated calcium channels*, Eur. J. Biochem. 264, 488-494 (1999)).

While some of the insecticidal peptide toxins isolated so far from scorpions and spiders offer promise, there still remains a significant need for compounds which display a wide differential in toxicity between insects and non-insects, and yet have significant insecticidal activity and a quick action.

The present inventors isolated, and structurally and functionally characterized, a novel insecticidal toxin, designated ω-atracotoxin-Hv2a, from the venom of the Australian funnel-web spider *H. versuta*. This ω-atracotoxin-Hv2a which is the subject of U.S. Pat. No. 6,583,264 B2 toxin is a highly potent and specific antagonist of insect calcium channels. The ω-atracotoxin-Hv2a toxin of the invention disclosed in U.S. Pat. No. 6,583,264 B2 shows no significant sequence similarity to any previously isolated insecticidal toxins, and no sequence or structural homology with the omega-atracotoxin-Hv1 family of insecticidal toxins previously isolated from *H. versuta* (See, Atkinson et al., Insecticidal toxins derived from funnel web spider (*Atrax* or *Hadronyche*) spiders, PCT/AU93/00039 (WO 93/15108) (1993); Fletcher et al., *The structure of a novel insecticidal neurotoxin*, *ω-atracotoxin-HV*1, *from the venom of an Australian funnel web spider*, Nature Struct. Biol. 4, 559-566 (1997); Wang et al., *Structure-function studies of* ω-*atracotoxin, a potent antagonist of insect voltage-gated calcium channels*, Eur. J. Biochem. 264, 488-494 (1999)).

The invention disclosed in U.S. Pat. No. 6,583,264 B2 is directed to the use of ω-atracotoxin-Hv2a, or the gene coding for the toxin, as a biopesticide, either alone or in combination with other insecticidal toxins or genes thereof. It further teaches the use of the toxin, or the gene coding for the toxin, as a screen for natural or non-natural compounds that specifically inhibit insect calcium channels. Furthermore, the patent's disclosure provides in the determination of the toxin's three-dimensional structure, a model for developing non-peptidic mimics of the toxin that could be used as foliar pesticide sprays.

As disclosed in the patent, there is provided a polypeptide toxin that is toxic to adult and/or larval insects having a molecular mass of approximately 4,478 Daltons and a length of 45 amino acid residues. The polypeptide is capable of forming three intrachain disulfide bonds. Activity of polypeptide as a toxin has been demonstrated by rapid paralysis of insects and/or potent inhibition of whole-cell calcium currents in isolated insect neurons. Phylogenetic specificity of the polypeptide toxin was demonstrated by minimal activity in rat or chicken nerve-muscle preparations and/or minimal antagonism of calcium channel currents in isolated rat neurons.

The preferred toxin as disclosed in U.S. Pat. No. 6,583,264 B2 is omega-atracotoxin-Hv2a (SEQ ID NO:1), abbreviated as omega-ACTX-Hv2a or ω-ACTX-Hv2a, as defined below:

```
SEQ ID NO: 1:
Leu-Leu-Ala-Cys-Leu-Phe-Gly-Asn-Gly-Arg-Cys-Ser-

Ser-Asn-Arg-Asp-Cys-Cys-Glu-Leu-Thr-Pro-Val-Cys-

Lys-Arg-Gly-Ser-Cys-Val-Ser-Ser-Gly-Pro-Gly-Leu-

Val-Gly-Gly-Ile-Leu-Gly-Gly-Ile-Leu

(LLACLFGNGR CSSNRDCCEL TPVCKRGSCV SSGPGLVGGI

LGGIL)
```

3. SUMMARY OF THE INVENTION

The instant inventors have now isolated and characterized additional spider venom peptides. The toxins of the present invention may be isolated from spider venom or chemically synthesized and oxidized/folded using similar techniques to those described previously for production of synthetic omega-atracotoxin-Hv1a (See, Atkinson et al., Insecticidal toxins derived from funnel web spider (*Atrax* or *Hadronyche*) spiders, PCT/AU93/00039 (WO 93/15108) (1993); Fletcher et al., *The structure of a novel insecticidal neurotoxin*, *ω-atracotoxin-HV*1, *from the venom of an Australian funnel web spider*, Nature Struct. Biol. 4, 559-566 (1997), both of which are incorporated by reference in their entirety herein). The toxins could also be prepared by using the techniques utilized in U.S. Pat. No. 6,583,264 B2 and namely from a synthetically constructed gene using recombinant DNA techniques as the authors have described previously for an unrelated protein (Riley et al., *Cloning expression, and spectroscopic studies of the Jun leucine zipper domain*, Eur. J. Biochem. 219, 877-886 (1994) which is incorporated in its entirety herein). A DNA probe coding for the amino sequence of the toxin may be used to isolate the gene coding for the protein or the corresponding preprotein or preproprotein using standard molecular biological techniques. The natural or synthetic gene(s) may be inserted into appropriate overexpression vectors for production of the toxin. In particular, the gene for the protein, preprotein, or preproprotein may be inserted into the genome of an appropriate insect vector, such as a baculovirus. Alternatively, transgenic plants may be constructed that express the toxin or the preprotein or preproprotein form of the toxin. Thus, the invention also provides insect viruses and plant species engineered to express the toxins of this invention.

The additional spider venom peptides are shown in the tables which follow. Table 1 provides the signal sequences and propeptide sequences with the overall percent identity provided relative to fw 217-fHV2 and Table 2 provides the mature toxic sequences with the percent sequence identity being given relative to ω-ACTX-Hv2a (SEQ ID NO:1). The Table 1-2 peptides, with the exception of ω-ACTX-Hv2a, are shown in SEQ ID NOS 2-35, respectively, in order of appearance.

| | | Signal Sequence[1,2] / Propeptide Sequence | % IdentitY |
|---|---|---|---|
| (SEQ ID NO: 2) | fw217-fHv2 | MKFSKLSLTLALILTQAIFVLCGKINEDFMKNDLESQALHDEIRKPIDSENPDTER | 100% |
| (SEQ ID NO: 4) | fw11-fHv2 | MKFSKLSLTLALILTQAIFVLCGKINEDFMKNDLESQALRDEURJOUDSEBODTER | 98% |
| (SEQ ID NO: 10) | fw214-fHv2 | MLFSKLSLTLALILTQAIFVLCGKINEDFMKNDLESQALHDEIRKPINSENPDTER | 98% |
| (SEQ ID NO: 16) | fw15-fHv2 | MKFSKLSLTLALILTQAIFVLCGKINEDFMKNDLESQALHDEIRKPINSENPDTER | 98% |
| (SEQ ID NO: 5) | fw218-fHv2 | MKFSKLSLTLALILTQAIFVLCGKINEDFMKNDLESHALHDEIRKPINSENPDTER | 96% |
| (SEQ ID NO: 6) | fw12-fHv2 | MKFSKLSLTLALILTQALFVLCGKINEDFMKNGLESQALHDEIRKPIDSENPDTER | 96% |
| (SEQ ID NO: 11) | fw229-fHv2 | MKFSKLSLTLALILTQALFVLCGKINEDFMKNGLESQALHDEIRKPIDSENPDTER | 96% |
| (SEQ ID NO: 15) | fw225-fHv2 | MKFSKLSLTLALILTQALFVLCGKINEDFMKNGLESQALHDEIRKPIDSENPDTER | 96% |
| (SEQ ID NO: 14) | fw130-hv2 | MKFSKLSLTLALILTQALFVLCGKINEDFMKNGLESQALHDEIRKPIDSENPDTER | 96% |
| (SEQ ID NO: 8) | fw131-hv2 | MKFSKLSLTLALILTGALFVLC-----DFMKNGLESQALHDEIRKSIDSENPDTER | 82% |
| (SEQ ID NO: 13) | fw128-hv2 | MKFSKLSLTLALILTQALFVLC-----DFMKNGLESQALHDEIRKPIDSENPDTER | 82% |
| (SEQ ID NO: 3) | fw112-mAr2 | MKFSKLSLTLALILTQALFVLCGKINEDFMKNGLESQTLHDEIRKPIDSENPDTER | 95% |
| (SEQ ID NO: 7) | fw126-hv2 | MKFSKLSLTLALILTQVIFVLCGKINEDFMKNGLESQALHDEIRKPIDSENPDTER | 96% |
| (SEQ ID NO: 12) | fw216-fHv2 | MKFSKLSLTLALILTQVLFVLCGKI-EDFMKNGLESQALHDEIRKPIDSENPDTER | 93% |
| (SEQ ID NO: 9) | fw118-mAr2 | MKFSLLSLTLALILTQVLFVLCGKINEDFMKNGLESQALHDEIRKPIDSENPDTER | 93% |
| (SEQ ID NO: 25) | fw56-fHv2_4009_ | MKFSKLSLTLALILTQALFVLCGKINEDFMENGLESHALHDEIRKPIDTEKADAER | 86% |
| (SEQ ID NO: 26) | fw69-hv2_4009_ | MKFSKLSLTLALILTQALFVLCGKINEDFMENGLESHALHDEIRKPIDTEKADAER | 86% |
| (SEQ ID NO: 24) | fw65-hv_4009_ | MKFSKLSLTLALILTQALFVLCGKINEDFMENGLESHALHDEIRKPIDTEKADAER | 86% |
| (SEQ ID NO: 31) | fw77-hv2_4009_ | MKFSKLSLTLALILAQAIFVLCGKINEDFMENGLESHALHDEIRKPIDTEKADAER | 86% |
| (SEQ ID NO: 19) | fw75-hv2_4009_ | MKFSKLSLTLALILTQALFVLCGKINEDFMEHGLESHALHDEIRKPIDTEKADAER | 84% |
| (SEQ ID NO: 22) | fw26-TO2 | MKFSKLSLTLALILTQALFVLCGKINEDFMEHGLESHALHDEIRKPIDTEKADAER | 84% |
| (SEQ ID NO: 20) | fw62-hv2_4009_ | MKFSKLSLTLALILTQALFVLCMKINEDFMENGLESHALHDEIRKPIDTEKADAER | 84% |
| (SEQ ID NO: 21) | fw55-fHv2_4009_ | MKFSKLSLTFALILTQALFVLCGKINEDFMDNGLESHALHDEIRKPIHTEKADAER | 82% |
| (SEQ ID NO: 23) | fw29-TO2 | MKFSKLSVTLALILTQTLIVLCGKINEDFMENGLESHALHDEIRKPIDTKAYDAER | 77% |
| (SEQ ID NO: 35) | fw60-Hv2_4009_ | MKFSKLSLTFALILTQTLIVLC-----DFMENGLESHALHDEIRKPIDTEKADAER | 73% |
| (SEQ ID NO: 32) | fw72-hv2_4009_ | MKFSKLSLTLALILTQALIVVCGKINEDFMENGLESHALHDEIRKPIDTEKADAER | 82% |
| (SEQ ID NO: 34) | fw27-TO2 | MKFSKLSLTLALILTQALIVVCGKINEDFMENGLESHALHDEIRKSIDTEKADAER | 80% |
| (SEQ ID NO: 33) | fw71-hv2_4009_ | MKFSKLSLTLALILTQALIVVCGKINEDFMENGLESHALHDEIRKPIDTEKADAER | 82% |
| (SEQ ID NO: 30) | fw58-Hv_4009_ | MKFSKLSLTLALILTQVLIVVCGKINEDFMENGLESHALHDEIRKPIDTEKADAER | 80% |
| (SEQ ID NO: 29) | fw68-hv2_4009_ | MKFSKLSLTLALILTQALIVLCGKINEDFMENGLESHALHDEIRKPLDTENPDTER | 88% |
| (SEQ ID NO: 17) | fw116-mAr2 | MKFSKLSITLAVILTQAVFVFCGMTNEDFMEKGLESNHLPDAIKKPVNSGKPDTKR | 66% |
| (SEQ ID NO: 18) | fw119-mAr2 | MKFSKLSITLAVILTQAVFVFCGMTNEDFMEKGLESNHLHDAIKKPVNSGKPDTER | 70% |
| (SEQ ID NO: 27) | fw121-mAr2 | MKFSKLSITLAVILTQAVFVFCGMTNEDFMEKGFKSNDLQYAIKQPVNSGKPDTER | 61% |
| (SEQ ID NO: 28) | fw5-mAr2 | MKFSKLSTTLVVILTQAVFVFCGMTNEDFMEKGFKSNDLQYAIRQPVNSGKPDTER | 61% |

| | | Mature Toxin Sequences[3] | % Identity |
|---|---|---|---|
| (SEQ ID NO: 1) | ω-ACTC-Hv2a | LLACLFGNGRCSSNRDCCELTPVCKRGSCVSSGPGLVGGILGGIL | 100% |
| (SEQ ID NO: 17) | fw116-mAr2 | LLDCVLS-RMCFSNANCCGLTPPCLMGLCVPNVGGLLGGIL---- | 53% |
| (SEQ ID NO: 18) | fw119-mAr2 | LLDCVLS-RMCSSDANCCGLTPICKMGLCVPNVGGLLGGIL---- | 53% |
| (SEQ ID NO: 27) | fw121-mAr2 | LLDCVLS-RVCSSDENCCGLTPICTMGLCVPNVGGLLGGLLS--- | 49% |
| (SEQ ID NO: 28) | fw5-mAr2 | LLDCVLS-RVCSSDENCCGLTPICTMGLCVPNVGGLLGGILS--- | 49% |
| (SEQ ID NO: 3) | fw122-mAr2 | LLDCLLDNRVCSSDRDCCGMTPSCTMGLCVPNVGGLVGGILG--- | 58% |
| (SEQ ID NO: 11) | fw229-fHv2 | LLDCLLDNRVCSSDRDCCGMTPSCTMGLCVPNVGGLVGDILG--- | 56% |
| (SEQ ID NO: 12) | fw216-fHv2 | LLDCLLDNRVCSSDKDCCGMTPSCTMGLCVPNVGGLVGGILG--- | 56% |
| (SEQ ID NO: 13) | fw128-hv2 | LLDCLLDNRVCSSDKDCCGMTPSCTMGLCVPNVGGLVGGILG--- | 56% |
| (SEQ ID NO: 14) | fw130-hv2 | LLDCLLDNRVCSSDKDCCGMTPSCTMGLCVPNVGGLVGGILG--- | 56% |
| (SEQ ID NO: 9) | fw118-mAr2 | LLDCLLDNRVCSSDKDCCGMTPSCTMGLCVPSVGGLVGGILG--- | 58% |
| (SEQ ID NO: 10) | fw214-fHv2 | LLDCLLDNRVCSSDKDCCGMTPSCTMGLCVPSVGGLVGGILG--- | 58% |
| (SEQ ID NO: 8) | fw131-hv2 | LLDCLLDNRVCSSDKDCCGMTPSCTMGLCVPSVGGLVGGILG--- | 58% |
| (SEQ ID NO: 7) | fw126-hv2 | LLDCLLDNRVCSSDKDCCGMTPSCTMGLCVPSVGGLVGGILG--- | 58% |
| (SEQ ID NO: 6) | fw12-fHv2 | LLDCLLDNRVCSSDKDCCGMTPSCTMGLCVPSVGGLVGGILG--- | 58% |
| (SEQ ID NO: 5) | fw218-fHv2 | LLDCLLDNRVCSSDKDCCGMTPSCTMGLCVPSVGGLVGGILG--- | 58% |
| (SEQ ID NO: 4) | fw11-fHv2 | LLDCLLDNRVCSSDKDCCGMTPSCTMGLCVPSVGGLVGGILG--- | 58% |
| (SEQ ID NO: 2) | fw217-fHv2 | LLDCLLDNRVCSSDKDCCGMTPSCTMGLCVPSVGGLVGGILG--- | 58% |
| (SEQ ID NO: 16) | fw15-fHv2 | LLDCLLDSRVCSSDKDCCGMTPSCTMGLCVPSVGGLVGGILG--- | 56% |
| (SEQ ID NO: 15) | fw225-fHv2 | LLDCLLDNRICSSDKDCCGMTPSCTMGLCVPNVGGLVGGILG--- | 56% |

-continued

| | | | |
|---|---|---|---|
| (SEQ ID NO: 19) | fw75-hv2_4009_ | LVDCVVNTLGCSSDKDCCGMTPSCTLGICAPSVRGLVGGLLGRAL | 49% |
| (SEQ ID NO: 26) | fw69-hv2_4009_ | LVDCVVNTLGCSSDKDCCGMTPSCTLGICAPSV-GLVGGLLGRAL | 49% |
| (SEQ ID NO: 20) | fw62-hv2_4009_ | LVDCVVNTLGCSSDKDCCGMTPSCTLGICAPSVGGLVGGLLGRAL | 49% |
| (SEQ ID NO: 22) | fw26-TO2 | LVDCVVNTLGCSSDKDCCGMTPSCTLGICAPSVGGLVGGLLGRAL | 49% |
| (SEQ ID NO: 24) | fw65-hv_4009_ | LVDCVVNTLGCSSDKDCCGMTPSCTLGICAPSVGGLVGGLLGRAL | 49% |
| (SEQ ID NO: 21) | fw55-fHv2_4009_ | LVDCVLNTLGCSSDKDCCGMTPSCTLGICAPSVGGLVGGLLGRAL | 49% |
| (SEQ ID NO: 31) | fw77-hv2_4009_ | VVDCVLNTLGCSSEKDCCGMTPSCTLGICAPSVGGLVGGLLGRAL | 47% |
| (SEQ ID NO: 23) | fw29-TO2 | VLDCVVNTLGCSSDKDCCGMTPSCTLGICAPSVGGLVGGLLGRAL | 49% |
| (SEQ ID NO: 35) | fw60-Hv2_4009_ | VLDCVVNTLGCSSDKDCCGMTPSCTLGICAPSVGGLVGGLLGRA- | 47% |
| (SEQ ID NO: 25) | fw56-fHv2_4009_ | VLDCVVNTLGCSSDKDCCGMTPSCTLGICAPSVGGLVGGLLGRAL | 49% |
| (SEQ ID NO: 30) | fw58-hV_4009_ | VLDCVVNTLGCSSDKDCCGMTPSCTLGICAPSVGGIVGGLLGRAL | 47% |
| (SEQ ID NO: 33) | fw71-hv2_4009_ | VLDCVVNTLGCSSDKDCCGMTPSCTLGICAPSVGGIVGGLLGRAL | 47% |
| (SEQ ID NO: 34) | fw27-TO2 | VLDCVVNTLGCSSDKDCCGMTPSCTLGICAPSVGGIVGGLLGRAL | 47% |
| (SEQ ID NO: 32) | fw72-hv2_4009_ | VLDCVVNILGCSSDKDCCGMTPSCTLGICAPSVGGIVGGLLGRAL | 47% |
| (SEQ ID NO: 29) | fw68-hv2_4009_ | QLDCVLNTLGCSSDKDCCGMTPSCTLGICAPNVGGLVGGLLGRAL | 47% |

[1]The C-terminal boundary of the Signal Sequence was predicted using the program SignalP (Nielsen et al., 1997);
[2]Percent identity is given relative to fw217-fHv2;
[3]Percent identity is given relative to w-ACTC-Hv2a The variants of ω-ACTX-Hv2a, which are provided are those wherein a "variant" is defined as a polypeptide that corresponds to or comprises a portion of ω-ACTX-Hv2a, or is homologous to ω-ACTX-Hv2a. For the purposes of this invention, "homology" between two peptide sequences connotes a likeness short of identity, indicative of a derivation of the first sequence from the second. In particular, a polypeptide is "homologous" to ω-ACTX-Hv2a if a comparison of their amino acid sequences reveals an identity greater than about 30% (which is usually sufficient to indicate structural homology). Such a sequence comparison can be performed via numerous computer algorithms in the public domain.

The invention, also provides a method of screening for, or designing, an antagonist of insect calcium channels. This method involves selecting or designing a substance which inhibits the binding of ω-ACTX-Hv2a, or a variant thereof as now disclosed, to insect calcium channels and testing the ability of the substance to act as an antagonist of insect calcium channels. The term "insect calcium channel" refers to any insect calcium channel that is inhibited by ω-ACTX-Hv2a or a variant thereof as now disclosed.

There is also provided by the present invention, a method of screening for substances for insecticidal potency and phylogenetic specificity, the method comprising: (a) measuring the ability of a substance to inhibit the binding of ω-ACTX-Hv2a, or the new variants thereof, to insect calcium channels; (b) measuring the ability of the substances to antagonize insect calcium channels; and (c) determining whether the substances have minimal activity against vertebrate calcium channels. Preferably the substance isolated by use of such methods have high phylogenetic specificity being defined herein as greater than 100-fold selectivity for insect over vertebrate calcium channels, and preferably greater than 1000-fold selectivity for insect over vertebrate calcium channels.

According to yet another embodiment of the present invention there is provided an insecticidal composition for delivering ω-ACTX-Hv2a, and the variants thereof, or an inhibitor of insect calcium channels, discerned by the methods described above. For example, where the toxin, the variant, or calcium channel antagonist can be expressed by an insect virus, the virus encoding the toxin, variant, or calcium channel antagonist can be applied to the crop to be protected. The virus may be engineered to express ω-ACTX-Hv2a, a ω-ACTX-Hv2a variant thereof as herein disclosed, or one of the calcium channel inhibitors either alone, in combination with one another, or in combination with other insecticidal polypeptide toxins that may result in synergistic insecticidal activity. The virus may be formulated in an agriculturally acceptable carrier, diluent and/or excipient. Suitable viruses include, but are not limited to, baculoviruses.

Alternatively, the crop itself may be engineered to express ω-ACTX-Hv2a, a ω-ACTX-Hv2a variant, or a calcium channel antagonist, discerned by the above described methods, either alone, in combination, or in combination with other insecticidal polypeptide toxins that may result in synergistic insecticidal activity. Crops for which this approach would be useful include cotton, tomato, green bean, sweet corn, lucerne, soybean, sorghum, field pea, linseed, safflower, rapeseed, sunflower, and field lupins.

Alternatively, the insecticidal agent may be delivered directly to the crop in an agriculturally acceptable carrier, diluent and/or excipient. Delivery could, for example, be in the form of a foliar spray. Insect infestation of crops may be controlled by treating the crops and/or insects with such compositions. The insects and/or their larvae may be treated with the composition, for example, by attracting the insects to the composition with an attractant.

4. BRIEF DESCRIPTION OF THE DRAWINGS

FIG. 1, panel a, is a reverse-phase high performance liquid chromatogram of whole venom isolated from *H. versuta* with the arrow indicating the retention time of ω-ACTX-Hv2a.

FIG. 1, panel b, is a reverse-phase high performance liquid chromatogram of ω-ACTX-Hv2a purified from the venom of *H. versuta.*

FIG. 4 is a schematic of the three-dimensional structure of ω-ACTX-Hv2a.

FIG. 5 illustrates the whole-cell calcium current measured in isolated bee brain neurons exposed to 1 nM and 10 nM ω-ACTX-Hv2a.

FIG. 6 illustrates the time course for the inhibition of whole-cell calcium channel currents in a bee brain neuron incubated with ω-ACTX-Hv2a.

5. DETAILED DESCRIPTION OF THE INVENTION

Figure 1:
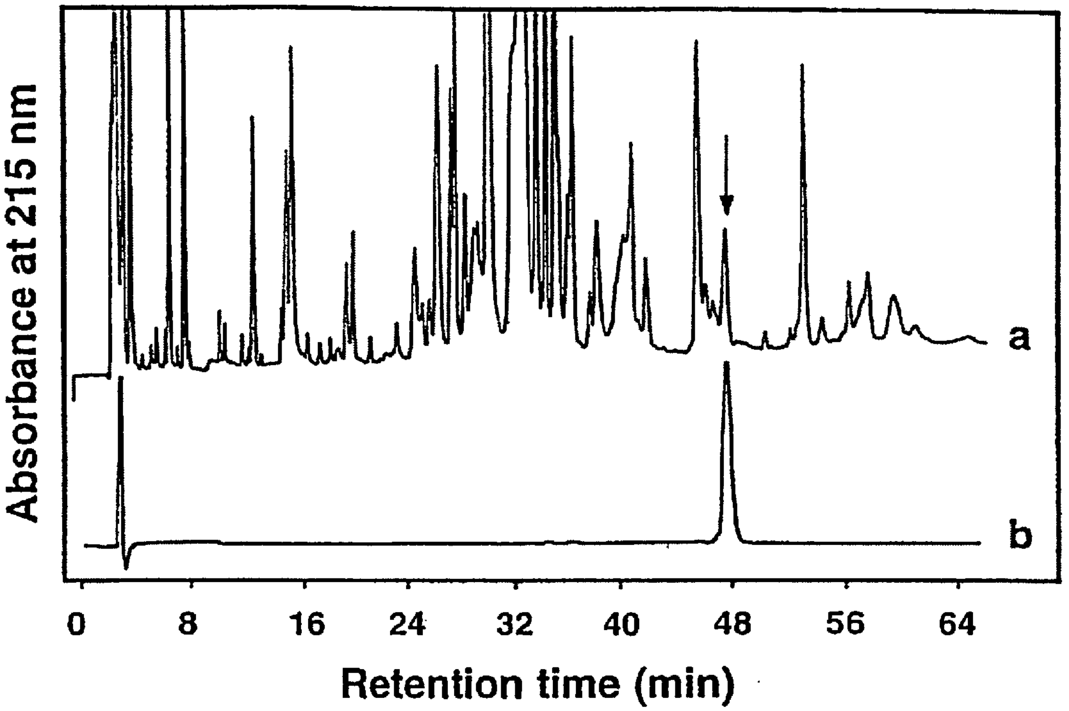

The inventors herein have in their earlier applications and U.S. Pat. No. 6,583,264 B2 disclosed an extremely potent and specific polypeptide-antagonist of insect calcium channels identified by SEQ ID NO:1 and referenced herein as "omega-ACTX-Hv2a" or "ω-ACTX-Hv2a". Such antagonist consists of forty-five amino acid residues, has a molecular mass of approximately 4,478 Daltons, and is capable of forming three intrachain disulfide bonds. Such antagonist has been found to be toxic to both adult and/or larval insects and to display more than 50,000-fold specificity for invertebrate over vertebrate voltage-gated calcium channels.

The inventors have now isolated and characterized a large number of different toxins from several different spiders. Such toxins or polypeptide antagonists (see Tables 1 and 2 above) have been found to be highly toxic to both adult and/or larval insects and to have minimal activity in other species.

SEQ ID NO:1 and the peptides shown in Tables 1-2 may be derived by chemically synthesizing the same and oxidizing/folding the peptide using similar techniques to those described previously for production of synthetic omega-atracotoxin-Hv1a (See, Atkinson et al., Insecticidal toxins derived from funnel web spider (*Atrax* or *Hadronyche*) spiders, PCT/AU93/00039 (WO 93/15108) (1993); Fletcher et al., *The structure of a novel insecticidal neurotoxin*, ω-*atracotoxin-HV*1, *from the venom of an Australian funnel web spider*, Nature Struct. Biol. 4, 559-566 (1997), both of which are incorporated by reference in their entirety herein). The polypeptide antagonist may also be derived by isolation from spider venom, in particular the venom of *Hadronyche versuta* and other Australian funnel-web spiders of the genera *Hadronyche* and *Atrax*.

The polypeptide antagonist SEQ ID NO:1 and the peptides as shown in Tables 1-2 may also be derived by constructing a synthetic gene coding for the polypeptide (e.g., based on computer-based back-translation), cloning the gene into an appropriate vector, transforming a cell line with the vector, causing the polypeptide to be expressed, and purifying the polypeptide. Expression systems may contain control sequences, such as promoters, enhancers and termination controls such as are known in the art for a variety of hosts (See, e.g, Sambrook et al., *Molecular Cloning: A Laboratory Manual*, Second Ed., Cold Spring Harbor Press (1989) which is incorporated herein in its entirety). The expression systems may also contain signal peptide and proprotein sequences that facilitate expression of the toxin gene and/or folding of the toxin.

The polypeptide toxins of the present invention may be prepared using recombinant DNA techniques such as described in Riley et al., *Cloning expression, and spectroscopic studies of the Jun leucine zipper domain*, Eur. J. Biochem 219, 817-886 (1994) (such reference being incorporated by reference in its entirely herein) which was authored by one of the present inventors.

The polypeptide toxins of the present invention may be prepared in both prokaryotic and eukaryotic systems. Constructs may be made wherein the coding sequence for the polypeptide is preceded by an operable signal peptide which results in secretion of the protein. The particulars for construction of expression systems and purification of peptides, and cleavage from fusion peptides are well known to those of ordinary skill in the art. Technology for introduction of DNA into cells includes four general methods: (1) physical methods such as microinjection, electroporation and the gene gun (See, e.g., Johnston et al., *Gene gun transfection of animal cells and genetic immunization*, Methods Cell. Biol. 43(A), 353-365 (1994)); (2) viral vectors (See, e.g., Eglitis et al., *Retroviral vectors for introduction of genes into mammalian cells*, Biotechniques 6(7), 608-614 (1988)); (3) chemical methods (See, e.g., Ausubel et al., *Current Protocols in Molecular Biology*, Vol. 1, Greene Publishing Associates/John Wiley & Sons (1993); Zatloukal et al., *Transferrinfection: A highly efficient way to express gene constructs in eukaryotic cells*, Ann. N.Y. Acad. Sci. 660, 136-153 (1992)), and (4) receptor-mediated mechanisms (See, e.g., Wagner et al., *Coupling of adenovirus to transferrin-polylysine/DNA complexes greatly enhances receptor mediated gene delivery and expression of transfected genes*, Proc. Natl. Acad. Sci. USA 89(13), 6099-6103 (1992)). As would be understood by one of ordinary skill in the art, minor modification of the primary amino acid sequence of SEQ ID NO:1 may result in a polypeptide as contemplated herein and as exemplified in Tables 1-2, which has substantially equivalent or enhanced activity as compared to SEQ ID NO:1. By "modification" of the primary amino acid sequence it is meant to include "deletions" (that is, polypeptides in which one or more amino acid residues are absent), "additions" (that is, a polypeptide which has one or more additional amino acid residues as compared to the specified polypeptide), "substitutions" (that is, a polypeptide which results from the replacement of one or more amino acid residues), and "fragments" (that is, a polypeptide consisting of a primary amino acid sequence which is identical to a portion of the primary sequence of the specified polypeptide). By "modification" it is also meant to include polypeptides that are altered as a result of post-translational events which change, for example, the glycosylation, amidation, lipidation pattern, or the primary, secondary, or tertiary structure of the polypeptide.

Preferred "substitutions" are those that are conservative, i.e., wherein the residue is replaced by another of the same general type. In making changes, the hydropathic index of amino acids may be considered (See, e.g., Kyte et al., J. Mol. Biol. 157, 105-132 (1982), herein incorporated by reference in its entirety). It is known in the art that certain amino acids may be substituted by other amino acids having a similar hydropathic index or score and still result in a polypeptide having similar biological activity. In making such changes, the substitution of amino acids whose hydropathic indices are within ±2 is preferred, those that are within ±1 are more preferred, and those within ±0.5 are even more preferred. Similarly, select amino acids may be substituted by other amino acids having a similar hydrophilicity, as set forth in U.S. Pat. No. 4,554,101 (herein incorporated by reference in its entirety). In making such changes, as with the hydropathic indices, the substitution of amino acids whose hydrophilicity indices are within ±2 is preferred, those that are within ±1 are more preferred, and those within ±0.5 are even more preferred.

Amino acid changes may be achieved by changing the codons of the DNA sequence making use, for example, of known redundancy in the code:

TABLE 1

| Amino Acid | Three-Letter Designation | Single Letter Designation | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glutamic Acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Preferably the variant is homologous to ω-ACTX-Hv2a. Sequence comparison can be performed via numerous computer algorithms that are well known to the skilled artisan. An homologous peptide may be produced in accordance with the present invention, for example, by conventional site-directed mutagenesis (which is one avenue for routinely identifying residues of the molecule that are functionally important or not), by random mutation (by "mutation" it is meant, an alteration in the primary structure of the polypeptide due to changes in the nucleotide sequence of the DNA which encodes it), by chemical synthesis, or by chemical or enzymatic cleavage of ω-ACTX-Hv2a, and other techniques known to those of ordinary skill in the art.

Recombinant DNA technology can be used to produce a recombinant expression vector virus of the polypeptide antagonists of the present invention. For example, a baculovirus expression vector such as the type disclosed in U.S. Pat. No. 4,879,236 (which patent is incorporated by reference in its entirety herein) may be produced. Other publications describing a method for recombinant protein expression using baculovirus vectors include Tomalski, et al., Nature 352, 82-85 (1991), Stewart et al., Nature 352, 85-88 (1991) and McCutchen et al., Biotechnology 9, 848-851 (1991). The recombinant expression vector virus could be applied to the area where the insect is a pest. When the virus is ingested by the insect its replication will begin. During replication, the gene for the insecticidally effective protein is expressed, resulting in the disablement or death of the insect. The virus may express ω-ACTX-Hv2a, or a variant thereof in accordance with this invention, or a calcium channel antagonist discovered by methods described herein. The virus could also be engineered to express ω-ACTX-Hv2a, or a variant thereof as described herein, or such calcium channel antagonist in the various combinations possible with one another, and furthermore in combination with other insecticidal polypeptide toxins. Such combinations may result in synergistic insecticidal activity. Hybrid bacterial cells, comprising a plasmid with the gene coding for polypeptide antagonists of the present invention may likewise be used to control insects in conformity with the present invention.

Insect calcium channel antagonists, viral vectors, and hybrid bacterial cells of the present invention may be applied in the form of a foliar spray comprising an agriculturally acceptable carrier. Crops for which this approach would be useful are numerous, and include, without limitation, cotton, tomato, green bean, sweet corn, lucerne, soybean, sorghum, field pea, linseed, safflower, rapeseed, sunflower, and field lupins. Such agents may also be applied to insects directly.

As would be understood by one of ordinary skill in the art, plants may be produced that express the polypeptide antagonists of the present invention. By "transgenic plant" it is meant any plant, or progeny thereof, derived from a "transformed plant" cell or protoplast, wherein the plant DNA (nuclear or chloroplast) contains an introduced exogenous DNA molecule not originally present in a native, non-transgenic plant of the same strain. Typical vectors useful for expression of genes in higher plants are well known in the art and include vectors derived from the tumor-inducing (Ti) plasmid of *Agrobacterium tumefaciens* (Rogers et al., Methods in Enzymol. 153, 253-277 (1987)), and pCaMVCN transfer control vector (available from Pharmacia, Piscataway, N.J.). Of course, as would be understood by one of ordinary skill in the art, other means of gene introduction into the cell may also be employed, such as electroporation (Fromm et al, *Expression of genes transferred into monocot and dicot plant cells by electroporation*, Proc. Natl. Acad. Sci. USA 82(17), 5824-5828 (1985)), polyethyleneglycol-mediated transformation of protoplasts (Ominrulleh et al., Plant Molecular Biology 21, 415-428 (1993)), desiccation/inhibition-mediated DNA uptake, agitation with silicon carbide fibers, by acceleration of DNA coated particles, injection into reproductive organs, and injection into immature embryos.

If an expression vector of the present invention is used to transform a plant, it is preferred that a promoter be selected that has the ability to drive expression in the plant. Promoters that function in plants are well known in the art. Exemplary tissue-specific promoters are corn sucrose synthetase 1 (Yang et al., Proc. Natl. Acad. Sci. USA 87, 4144-4148 (1990)), cauliflower mosaic virus (CaMV 35S) promoter, S-E9 small subunit RuBP carboxylase promoter, and corn heat shock protein (Odell et al., Nature 335, 810 (1985)). The choice of which expression vector, and ultimately to which promoter a polypeptide coding region is operatively linked, depends directly on the functional properties desired, for example, the location and timing of protein expression and the host cell to be transformed. In a preferred embodiment, the vector used to express the polypeptide includes a selection marker that is effective in a plant cell. Transformation vectors used to transform plants and methods of making those vectors are described, for example, in U.S. Pat. Nos. 4,971,908, 4,940,835, 4,769,061 and 4,757,011, the disclosures of which are incorporated in their entirety herein by reference.

The present invention also encompasses DNA sequences encoding for SEQ ID NO:1 and the variants thereof as herein disclosed and contemplated. The DNA sequences encoding for such active polypeptide sequences allow for the preparation of relatively short DNA (or RNA) sequences having the ability to specifically hybridize to such gene sequences. The short nucleic acid sequences may be used as probes for detecting the presence of complementary sequences in a given sample, or may be used as primers to detect, amplify or mutate a defined segment of the DNA sequences encoding for SEQ ID NO:1, and variants thereof. A preferred nucleic acid sequence employed for hybridization studies is at least 14 nucleotides in length to ensure that the fragment is of sufficient length to form a stable and selective duplex molecule. Such fragments may be prepared by, for example, directly synthesizing the fragment by chemical means, by application of nucleic acid reproduction technology, such as the PCR technology (described in U.S. Pat. Nos. 4,683,195 and 4,683,202, herein incorporated in their entirety by reference), or by excising selected nucleic acid fragments form recombinant plasmids containing appropriate inserts and suitable restriction sites.

Improved methods for screening for and/or designing antagonists of insect calcium channels are also provided. Given the large difference between the binding constants of ω-ACTX-Hv2a or variant thereof with respect to invertebrate versus vertebrate calcium channels, in particular those calcium channels associated with the insect neuronal system, ω-ACTX-Hv2a or a variant as disclosed herein may be effectively used in screening procedures to identify new antagonists of insect calcium channels. Using conventional structure-activity analysis of identified insect calcium channel antagonists, routes of chemical design of other more potent antagonists may be pursued based on the identified antagonists.

One method for isolating compounds having insect calcium channel antagonist activity comprises the steps of: preparing an invertebrate cellular preparation having a substantial number of unbound calcium channels; adding an amount of ω-ACTX-Hv2a or a variant as herein disclosed effective to substantially bind all of the calcium channels of the invertebrate cellular preparation; selecting a test compound; adding the test compound to the invertebrate cellular preparation bound with ω-ACTX-Hv2a or the variant as herein disclosed; measuring the amount of ω-ACTX-Hv2a or variant released by the addition of the test compound.

Another method for isolating compounds having insect calcium channel antagonist activity comprises the steps of preparing an invertebrate cellular preparation having a substantial number of unbound calcium channels; selecting a test compound; adding the test compound to the invertebrate cellular preparation at a set concentration; allowing the test compound to incubate for a period of time sufficient to allow the test compound to bind with the calcium channels of the preparation; washing the invertebrate cellular preparation which was incubated with the test compound so as to remove any unbound test compound; adding an amount of ω-ACTX-Hv2a or a variant thereof as for example set forth in Tables 1-2 sufficient to bind all of the calcium channels of the untreated invertebrate cellular preparation; measuring the amount of test compound displaced by the addition of the ω-ACTX-Hv2a or the selected variant.

Preferably, any antagonist identified by the screening procedure will bind strongly to insect calcium channel(s) such that the dissociation constant ($K_d$) for its interaction with the calcium channel(s) is less than $10^{-7}$ M and more preferably less than $10^{-9}$ M. Preferably, the activity of the test compound against vertebrate calcium channels is then determined so as to discern the relative selectivity of the compound. In a preferred embodiment, phylogenetic specificity is greater than 100-fold for insect over vertebrate calcium channels, and more preferably greater than 1000-fold. As would be recognized by one of ordinary skill in the art, other types of competitive assays and pharmacological activity screening procedures known in the art may be adapted to utilize ω-ACTX-Hv2a or a variant in accordance with this invention to provide for improved screening of compounds for invertebrate calcium channel antagonism.

Test compounds may comprise a compound from an archive of natural compounds or from combinatorial libraries of peptidic and non-peptidic compounds.

Libraries of mutated toxins for the purposes of screening may be obtained by in vitro evolution of a gene for ω-ACTX-Hv2a or a variant, as described previously for unrelated proteins (Stemmer, *DNA shuffling by random fragmentation and re-assembly; in vitro recombination for molecular evolution*, Proc. Ned. Acad. Sci. 91, 10747-10751 (1994); Stemmer, *Rapid evolution of a protein in vitro by DNA shuffling*, Nature 370, 389-391 (1994); Zhang et al., *Directed evolution of a fucosidase from a glactosidase by DNA shuffling and screening*, Proc. Natl. Acad. Sci. USA 94, 4504-4509 (1997), all of which are incorporated by reference in their entirety herein). This could be done using error-prone PCR of the entire ω-ACTX-Hv2a or variant gene or digestion of the ω-ACTX-Hv2a or variant gene with an appropriate enzyme followed by error-prone PCR reconstruction of the entire gene sequence. These error-prone PCR procedures could also be applied to the complete preproprotein gene sequence for ω-ACTX-Hv2a or a contemplated variant (Table 1-2). The library of mutant ω-ACTX-Hv2a or variant gene sequences could then be used to generate a series of ω-ACTX-Hv2a variant antagonists. These antagonists may then be screened for their ability to inhibit the binding of ω-ACTX-Hv2a, or selected variant thereof, to insect calcium channels, or directly for their ability to inhibit insect calcium channels. Screening may be performed, for example, by phage display of a mutant gene library followed by selection of phage particles that bind tightly to insect calcium channels, or phage particles that inhibit the binding of ω-ACTX-Hv2a or the selected variant thereof, to insect calcium channels. As would be understood by one of ordinary skill in the art, a mutant gene library could also be constructed by other standard molecular biological methods such as oligonucleotide cassette mutagenesis or construction of synthetic genes with certain nucleotide positions randomised.

The three-dimensional structure of ω-ACTX-Hv2a, and variants thereof which have been elucidated by the present inventors as set forth in the tables and drawings, may also be used to search structure libraries for (or to design) either peptidic or non-peptidic compounds that resemble the key structural elements of ω-ACTX-Hv2a, particularly those regions found to be critical for activity by mutagenesis/truncation/modification experiments. These compounds could then be tested for their ability to inhibit the binding of ω-ACTX-Hv2a, or the variant thereof, to insect calcium channels.

The ω-ACTX-Hv2a or variant thereof in accordance with the invention used in a competitive assay may be radioactive or fluorescently labeled, all of which fall within the scope of the present invention. Screening of test compounds may be performed using either native or recombinantly produced calcium channels, or structurally-modified calcium channels.

The present inventors have found that acutely isolated cockroach and bee brain neurons are particularly suitable to provide the basis for a sensitive electrophysiological assay for assaying substances that interfere with the ability of ω-ACTX-Hv2a or its variants to inhibit insect calcium channels, while a variety of mouse sensory ganglion neurons are suitable to provide the basis for a sensitive electrophysiological assay for testing the ability of compounds to inhibit vertebrate calcium channels. It will be appreciated, however, that other insect and vertebrate cells or cell lines would also be suitable for use in this aspect of the present invention. For example, transient expression of cloned insect calcium channels in suitable cell lines or oocytes could form the basis of a suitable assay system.

Now turning to several examples that illustrate particular compositions and methods within the scope of the present invention. Such examples, and the figures associated therewith, are presented in order to make certain aspects of the present invention more clearly understood, and are not intended to limit the scope of the invention as described herein in any manner.

Example 1

Elution and Purification of Polypeptide Toxin from *H. versuta* Whole Venom

Lyophilized crude venom (1.25 mg) was dissolved in 50 μl distilled water, loaded onto a Vydac C18 analytical reverse-phase HPLC column (4.6×250 mm, 5 μm pore size), and eluted at a flow rate of 1 ml $min^{-1}$ using a gradient of 5-25% Buffer B (0.1% TFA in acetonitrile) over 22 min, followed by a gradient of 25-50% Buffer B over 48 min. Buffer A was 0.1% TFA in water. FIG. 1 depicts two reverse-phase HPLC chromatograms. FIG. 1*a* is a reverse-phase HPLC chromatogram of the whole venom isolated from *H. versuta*. The elution position of the polypeptide toxin referred to as ω-ACTX-Hv2a (retention time of approximately 48 min) is marked with an arrow. FIG. 1*b* is a reverse-phase HPLC chromatogram of the ω-ACTX-Hv2a that had been purified from *H. versuta* venom using standard chromatographic purification techniques.

Example 2

Determination of Primary Structure of ω-ACTX-Hv2a

Figure 2:
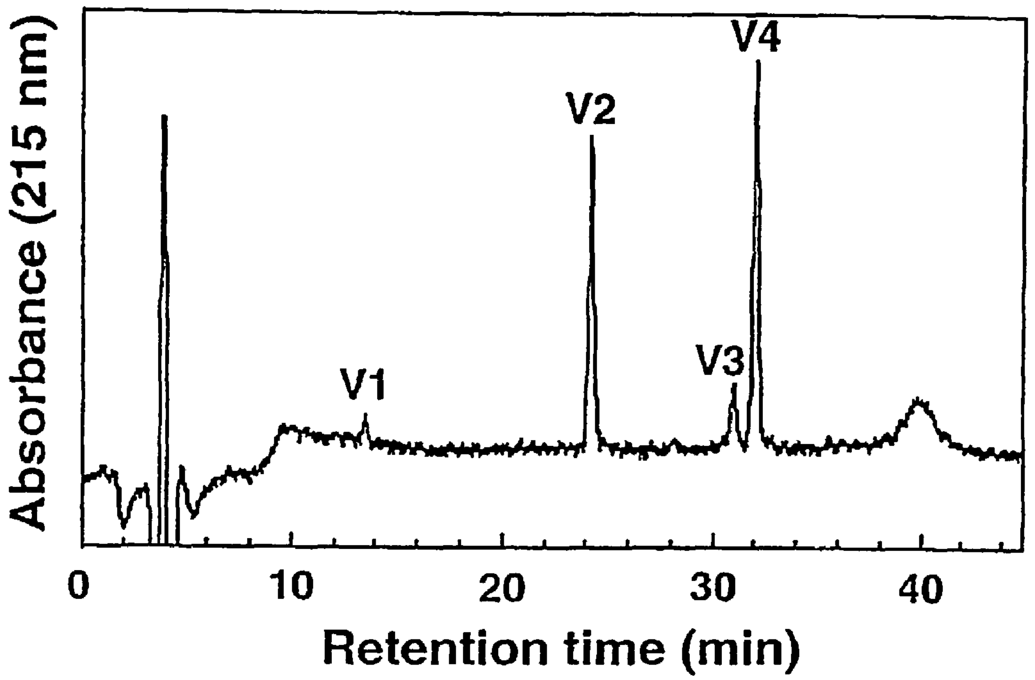
FIG. 2 is a reverse-phase high performance liquid chromatogram of ω-ACTX-Hv2a that has been reduced, alkylated with vinylpyridine, then treated with *Staphylococcus aureaus* strain V8 type XVII-B protease.

Isolated ω-ACTX-Hv2a (50 μg) was reduced and pyridylethylated, then digested with *Staphylococcus aureus* strain V8 type XVII-B protease [EC 3.4.21.19] for 6 hours at a toxin:protease ratio of 100:1 and a temperature of 37° C. The reaction was carried out in 50 mM Tris buffer, pH 7.8. The resulting peptide fragments (labeled V1-V4) were applied to a Vydac C18 analytical reverse-phase HPLC column (4.6×250 mm, 5 μm pore size), and eluted at a flow rate of 1 ml $min^{-1}$ using a gradient of 5-60% Buffer B (0.1% TFA in acetonitrile) over 40 min. Buffer A was 0.1% TFA in water. FIG. 2 shows a reverse-phase HPLC chromatogram of the fragments resulting from digestion of ω-ACTX-Hv2a.

Figure 3:
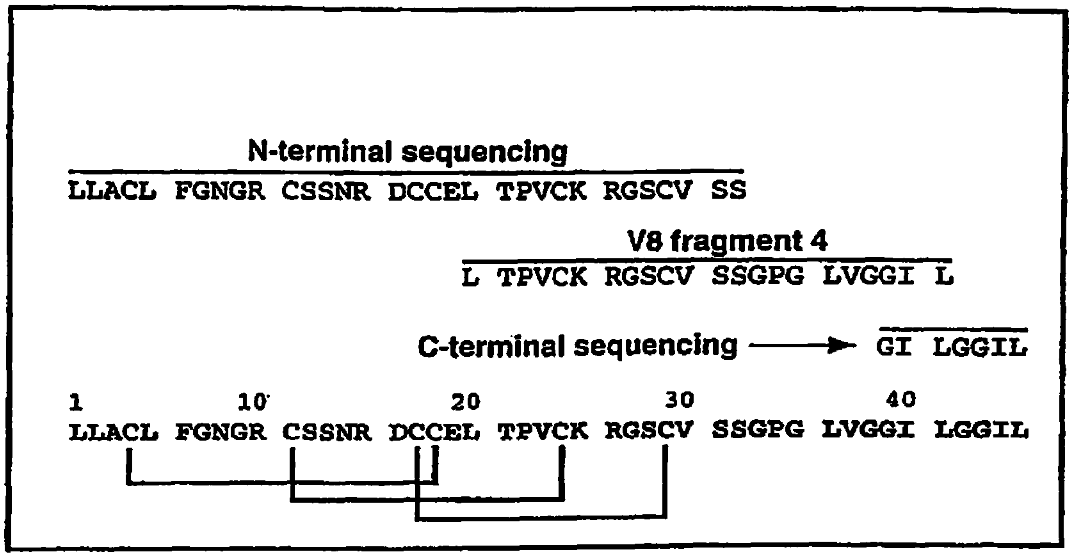
FIG. 3 depicts the primary structure of ω-ACTX-Hv2a (SEQ ID NO: 1) as elucidated from N-terminal and C-terminal amino acid sequencing data. The peptide fragments correspond to residues 1-32, 20-41 and 39-45 of SEQ ID NO: 1, respectively, in order of appearance.

The primary structure of ω-ACTX-Hv2a was reconstructed from N-terminal and C-terminal sequencing of the complete toxin as well as sequencing of various fragments obtained from digestion with V8 protease. The primary structure is shown in FIG. 3 using the internationally recognized one-letter abbreviations for each of the amino acids. Such structure as shown was reconstructed from N-terminal and C-terminal sequencing as well as V8 fragment 4 obtained by digestion with V8 protease. The disulfide-bonding pattern of ω-ACTX-Hv2a, as determined from the three-dimensional structure (see FIG. 4), is indicated by the heavy lines.

Example 3

Determination of Three-Dimensional Structure of ω-ACTX-Hv2a

Figure 4:
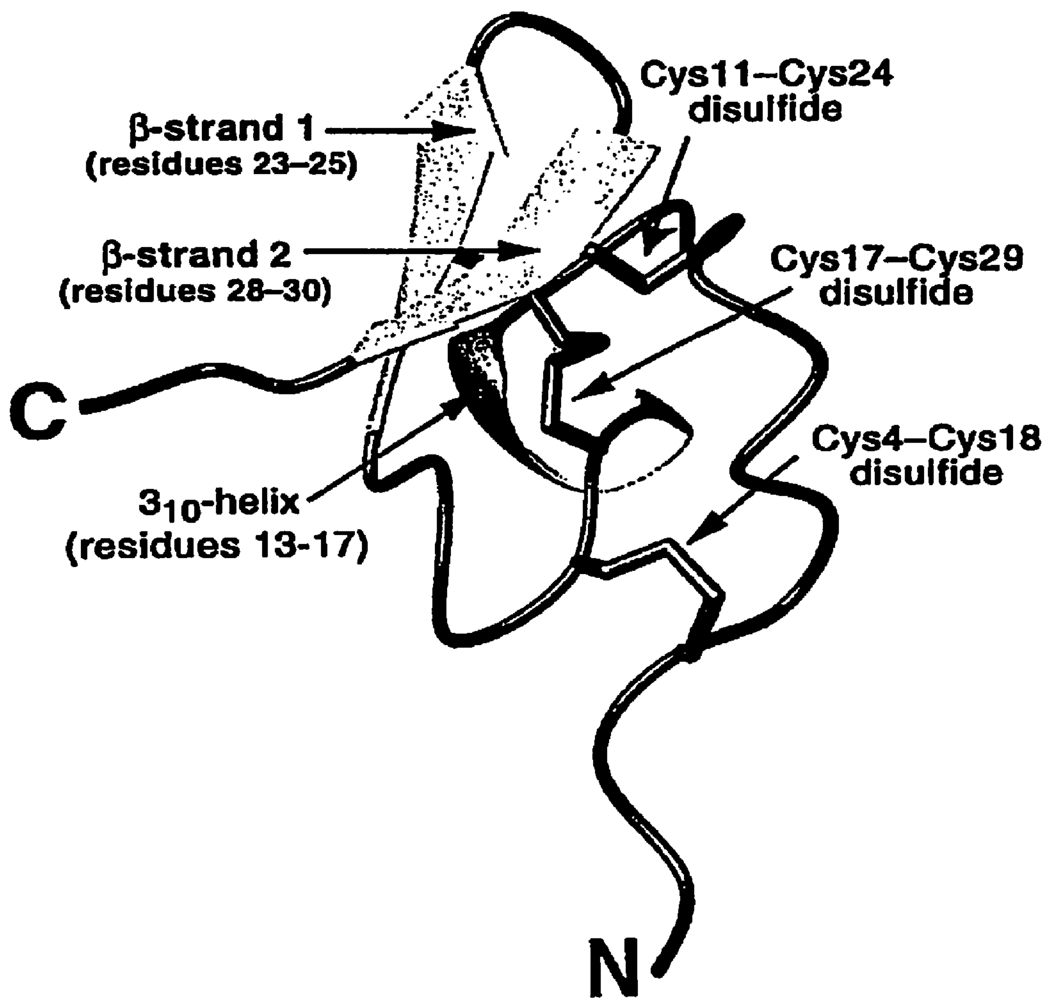

The three-dimensional structure of ω-ACTX-Hv2a was determined using standard two-dimensional homonuclear nuclear magnetic resonance (NMR) spectroscopy techniques familiar to those skilled in the art (see, Fletcher et al., *The structure of a novel insecticidal neurotoxin*, *ω-ACTX-Hv*1, *from the venom of an Australian funnel web spider*, Nature Struct. Biol. 4, 559-566, 1997; Wüthrich, *NMR of Proteins and Nucleic Acids* (John Wiley & Sons, Inc., New York, 1986), both of which are incorporated in their entirety herein). FIG. 4 is a schematic of the three-dimensional solution structure of residues 1-32 of ω-ACTX-Hv2a; residues 33-45 have no preferred conformation in solution. The structure contains a $3_{10}$ helix encompassing residues 13-17, an antiparallel β-hairpin comprising two β-strands (β strand 1=residues 23-25, β strand 2=residues 28-30), and three disulphide bonds (Cys4-Cys18, Cys11-Cys24, and Cys17-Cys29). These structural features are all delineated by arrows in FIG. 4.

Example 4

Effect of ω-ACTX-Hv2a on Whole-Cell Calcium Channel Currents in Isolated Bee Neurons Neurons were isolated from the brains of adult European honey bees, *Apis mellifera*, as the authors have described previously (see, Wang et al., *Discovery and characterization of a family of insecticidal neurotoxins with a rare vicinal disulfide bond*, Nature Struct. Biol. 7, 505-513, which is incorporated in its entirety herein). Standard whole cell voltage clamp recordings were made of bee brain calcium channel ($I_{Ca}$), sodium channel ($I_{Na}$) and potassium channel ($I_K$) currents at ambient temperature (22-24° C.). For bee neurons, recordings were made with fire polished borosilicate pipets of ~6 M resistance when filled with intracellular solution of either of the following compositions (mM): CsCl 120, NaCl 5, MgATP 5, $Na_2$GTP 0.3, EGTA 10, $CaCl_2$ 2 and HEPES 10, pH 7.3 (for $I_{Na}$ and $I_{Ca}$) or KF 130, EGTA 10, $CaCl_2$ 2 and HEPES 10, pH 7.3 for recording $I_K$. For recordings of $I_{Ca}$ and $I_{Na}$ the external solution consisted of NaCl 135, tetraethylammonium chloride (TEACl) 20, CsCl 5, $BaCl_2$ 5, HEPES 10, glucose 10, BSA 0.05%, pH 7.3. For $I_K$ recording the external solution consisted of (mM) NaCl 130, KCl 20, $CaCl_2$ 2.5, $MgCl_2$ 1.5, HEPES 10, glucose 10, BSA 0.05%, pH 7.3.

Neurons were voltage clamped at −90 mV and currents evoked by stepping the membrane potential from −60 to +60 mV. Toxin effects on $I_{Ca}$, and $I_{Na}$, were tested at the potential with largest inward current, usually −10 or 0 mV. In bee neurons the peak inward currents were usually abolished by 100 μM $Cd^{2+}$, suggesting that the current was largely carried by $Ca^{2+}$ channels. In a few bee neurons there was a rapidly activating, transient and $Cd^{2+}$-insensitive current which was blocked completely by tetrodotoxin (TTX, 1 μM).

Figure 5:
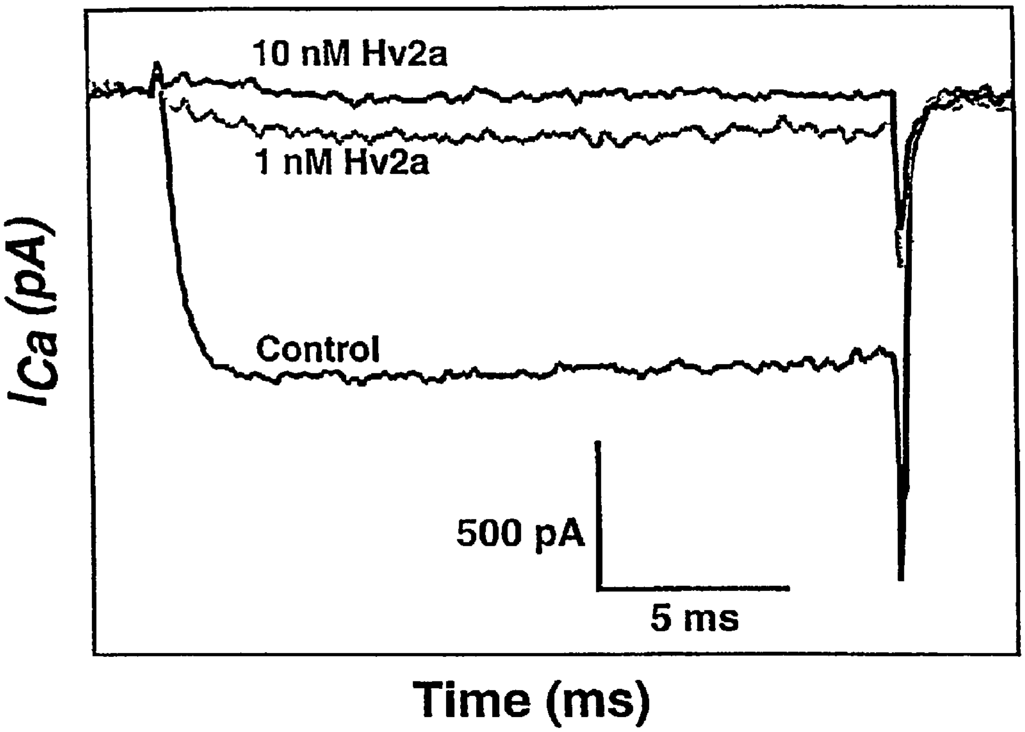

FIG. 5 illustrates the effect of ω-ACTX-Hv2a on whole-cell calcium channel currents in such isolated bee brain neurons. The figure shows the whole-cell calcium current obtained from a bee brain neuron in the absence ("control") or presence of 1 nM or 10 nM ω-ACTX-Hv2a. Application of ω-ACTX Hv2a (10 μM to 100 nM) inhibited calcium channel currents in all neurons examined (n=37). The almost complete abrogation of calcium channel currents by these low concentrations of toxin indicates that most, if not all, bee brain calcium channels are sensitive to ω-ACTX-Hv2a. This contrasts with ω-ACTX-Hv1a, which inhibits whole-cell calcium channel currents in isolated cockroach neurons by only 25±10% at a concentration of 100 nM (see FIG. 6 in Fletcher et al., *The structure of a novel insecticidal neurotoxin*, *ω-ACTX-Hv*1, *from the venom of an Australian funnel web spider*, Nature Struct. Biol. 4, 559-566, 1997).

Figure 6:
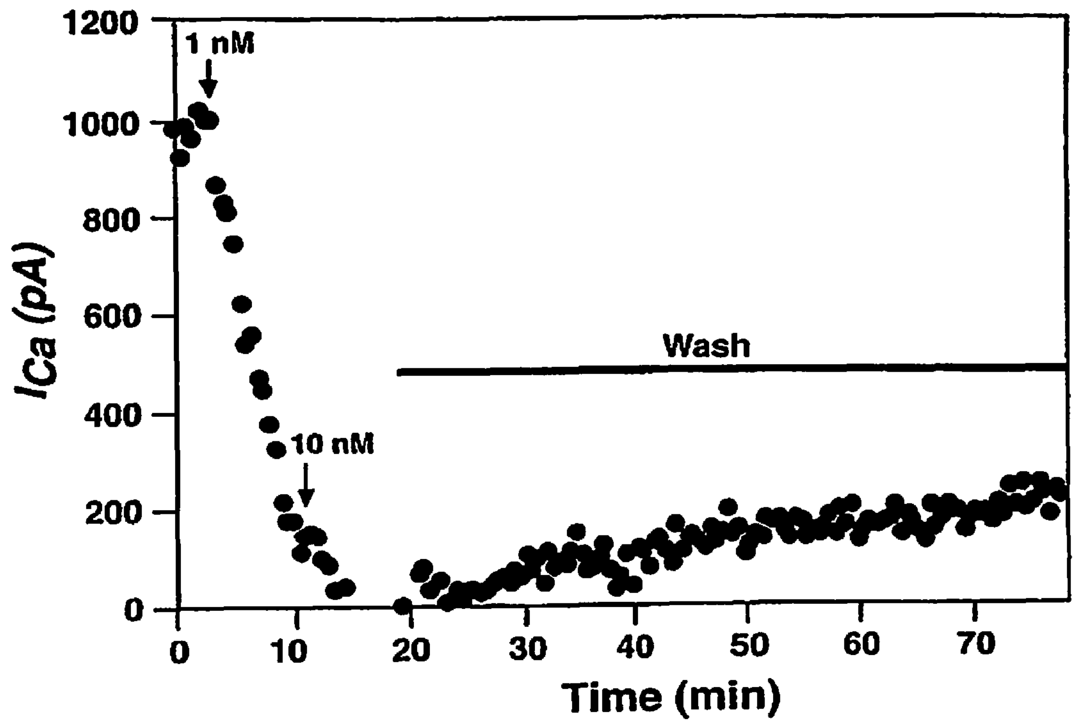

FIG. 6 illustrates the time course for the inhibition of whole-cell calcium channel currents in a bee brain neuron following addition of 1 nM and 10 nM ω-ACTX-Hv2a: the effect is rapid and only very slowly reversible as indicated by the protracted recovery of channel activity after initiating a wash step (indicating by the solid horizontal line). The rapid calcium channel inhibition and slow recovery observed in these electrophysiological experiments is consistent with the phenotypic effects observed when the toxin is injected into house crickets (*Acheta domesticus* Linnaeus). Injection into crickets causes immediate paralysis with a $PD_{50}$ (the dose required to paralyse 50% of injected insects) of 160±9 pmol $g^{-1}$ and a mean paralysis time of 4-5 h at a dose of 250-500 pmol $g^{-1}$. Injection of crickets with a second dose (250-500 pmol $g^{-1}$) of toxin prior to reversal of paralysis was lethal. In striking contrast, the toxin did not provoke any adverse effects when injected subcutaneously into newborn BALB/c mice (3.1±0.2 g, n=3) at doses up to 800 pmol $g^{-1}$, which is 5-fold higher than the $PD_{50}$ in crickets.

Example 5

Comparison of the Effects of ω-ACTX-Hv2a and ω-agatoxin-IVA on Whole-Cell Calcium Channel Currents in Isolated Bee Neurons and Mouse Trigeminal Neurons Bee brain neurons were isolated as described in Example 4 above. Mouse trigeminal ganglion neurons were isolated by gentle trituration of minced ganglia following a 20-min treatment at 34 C with papain (20 units $ml^{-1}$) in a HEPES buffered saline (HBS) solution of composition (in mM): NaCl 140, KCl 2.5, $CaCl_2$ 2.5, $MgCl_2$ 1.5, HEPES 10, glucose 10, pH 7.3. Standard whole cell voltage clamp recordings were made of bee brain calcium channel ($I_{Ca}$), sodium channel ($I_{Na}$) and potassium channel ($I_K$) currents and mouse sensory neuron $I_{Ca}$ and $I_{Na}$ at ambient temperature (22-24 C). The same internal solution as described for the bee brain recordings in Example 4 was used for recordings of mouse sensory neuron $I_{Ca}$ and $I_{Na}$; the electrodes had a resistance of 1-2 M. The $I_{Ca}$ external solution for the mouse neuron recordings contained (mM): TEACl 140, CaCl2 2.5, CsCl 2.5, HEPES 10, glucose 10, BSA 0.05%, pH 7.3, while $I_{Na}$, were recorded in HBS.

Neurons were voltage clamped at −90 mV and currents evoked by stepping the membrane potential from −60 to +60 mV. In mouse sensory neurons, the peak inward currents evoked in the presence of potassium and sodium channel blockers were abolished by 30 μM $Cd^{2+}$. The inward currents recorded in HBS consisted of both TTX-sensitive and TTX-resistant components. Toxin effects on bee brain $I_K$ were determined over a range of membrane potentials (from −40 to +60 mV). Data were collected and analysed as described previously (see, Fletcher et al, *The structure of a novel insecticidal neurotoxin*, ω-*ACTX-Hv*1, *from the venom of an Australian funnel web spider*, Nature Stmt. Biol. 4, 559-566, 1997).

Figure 7:
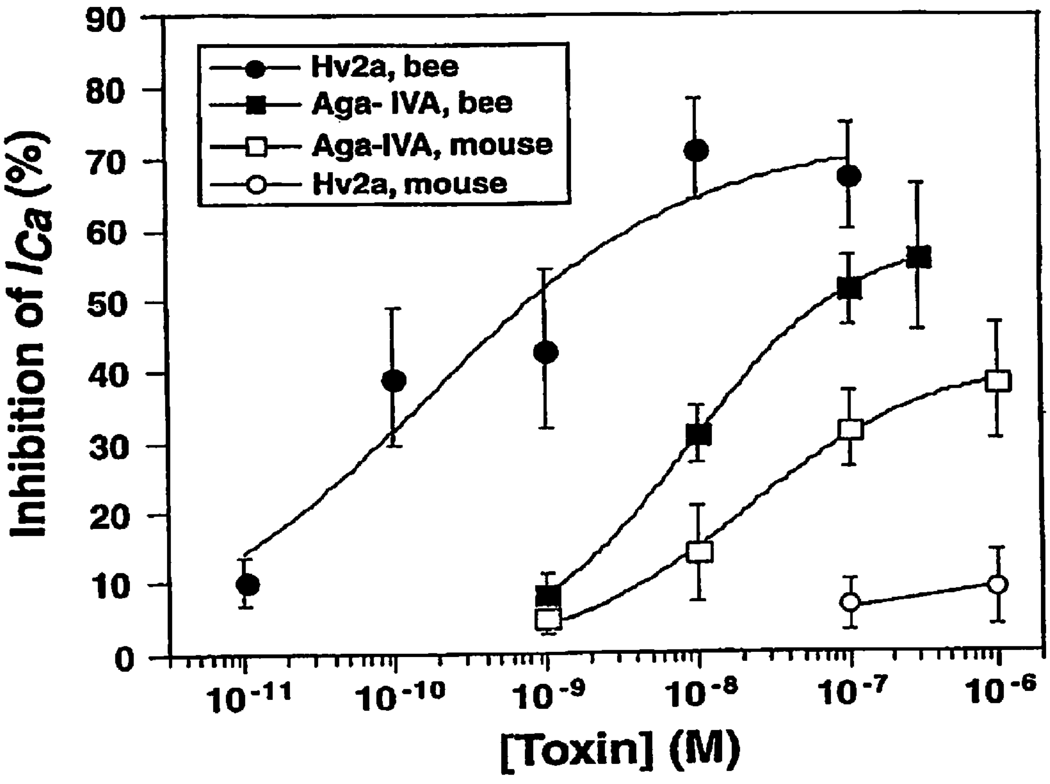
FIG. 7 illustrates dose-response curves for inhibition of whole-cell calcium currents by ω-ACTX-Hv2a and ω-agatoxin-IVA (from the American funnel-web spider *A. aperta*) in bee brain and mouse trigeminal neurons.

FIG. 7 shows that the $EC_{50}$ for ω-ACTX-Hv2a inhibition of $I_{Ca}$ was ~150 pM (see data indicated by filled circles), with maximum inhibition occurring at concentrations >10 nM. Application of the American funnel-web spider toxin ω-agatoxin-IVA (ω-Aga-IVA; see filled squares in FIG. 7), the prototypic antagonist of vertebrate P-type voltage-gated calcium channels (see, Mintz et al., *P-type calcium channels blocked by the spider toxin omega-Aga-IVA*, Nature 355, 827-829, 1992), also inhibited $I_{Ca}$ in all bee neurons examined (n=19), but the $EC_{50}$ (10 nM) and the concentration required for maximum inhibition (>100 nM) were both significantly higher than for ω-ACTX-Hv2a.

In striking contrast, superfusion of high concentrations of ω-ACTX-Hv2a (1 μM, n=10) for 5 min had virtually no effect on $I_{Ca}$ in mouse sensory neurons (see unfilled circles in FIG. 7), whereas application of ω-Aga-IVA inhibited a component of $I_{Ca}$ in all mouse sensory neurons with an $EC_{50}$ of about 20 nM (maximum $I_{Ca}$ inhibition ~40%; see unfilled squares in FIG. 7). ω-ACTX-Hv2a (100 nM) did not inhibit the TTX-sensitive $I_{Na}$ of bee brain neurons ($I_{Na}$ was 98±4% of control, n=4), nor did it significantly affect $I_{Na}$ in mouse sensory neurons ($I_{Na}$ was 97±3% of control with ω-ACTX-Hv2a=1 μM, n=5). ω-ACTX-Hv2a (10 nM, n=1; 100 nM, n=5) had no effect on bee brain $I_K$ at any potential when neurons were stepped from −90 mV to between −40 and +60 mV.

Example 6

Australia. A female *Hydronyche infensa* species was collected from the city of Toowoomba, Queensland. A female *Hydronyche versuta* was obtained from the Blue Mountains of New South Wales, Australia. Male and female *Atrax robustus* species were collected from collected from the Sydney area of New South Wales, The specimens were housed in airtight collection jars until extraction of venom glands. The Funnel-web spiders were cooled to −20° C. for 40-60 minutes. Venom glands were independently dissected from each specimen (*H. infensa. H. versuta*. male *A. robustus*. and female *A. robustus*). Each pair of venom glands was independently placed in extraction buffer (Pharmacia).

Preparation of cDNA

Immediately following venom gland isolation, polyA+ mRNA was prepared using QuickPrep Micro mRNA Purification Kit (Amersham Pharmacia Biotech). The purified mRNA samples were washed with 80% ethanol and dried with a Speedvac. 10 μl of RNAse-free distilled water obtained from cDNA Synthesis Kit (Pharmacia) was used to rehydrate the mRNA samples. The purified mRNA samples were stored at −20° C.

Thereafter, cDNA libraries were constructed using the Marathon cDNA Amplification Kit (CLONTECH). From the adapted mRNA template, single strand cDNA was constructed using Superscript III reverse transcriptase (Life Technologies, Inc) and Echoclonanch-2 primer, a poly(dT) anchor primer ($GGGCAGGT_{17}$) (SEQ ID NO: 36) Second strand synthesis was carried out according to the kit specifications. cDNA products were purified using Concert Rapid PCR Purification kit (GIBCO). The double stranded cDNA was eluted with 50 μl~70° C. TE buffer (10 mM Tris-CI, 1 mM EDTA, pH8.0).

The Marathon cDNA Amplification adaptor (CLONTECH) was then ligated to the double stranded cDNA. The ligation reaction was allowed to take place at 16° C. overnight. After overnight ligation, the sample was precipitated using 10 μl of a 1 to 20 dilution of glycogen, 10 μl 3M sodium acetate pH 5.2, and 100 μl 100% cold ethanol. Subsequently, the sample was washed with 80% ethanol and dried for 10 minutes prior to resuspension in 200 μl TE buffer.

Primer Design

In order to obtain leader sequence information, 5' RACE (Rapid Amplification of cDNA Ends) was used. Frohman, M. A., M. K. Dush, and G. R. Martin, *Rapid production of full-length cDNAs from rare transcripts: amplification using a single gene-specific oligonucleotide primer*. Proc Natl. Acad. Sci. USA, 1988. 85(23): p. 8993-9002. Redundant polymerase chain reaction (PCR) primers were designed for this technique. The primers were designed based on the N-terminal amino acid sequence of the w-ACfX-Hv2a mature toxin. The redundant primers were used in conjunction with a.5' universal. adaptor primer (EchoAP1) in order to obtain unknown leader sequence information. 3' RACE PCR primers were designed from the cDNA leader sequence data obtained from the '5' RACE. 3' RACE PCR primers were used in combination with a universal adaptor oligo d(T)

primer (CLONTECH) to generate gene products that have a signal sequence that is homologous with that of w-ACTX-Hv2a. All primers not included in kits were constructed by PROLIGO Ltd.

PCR Amplifications

PCR was conducted using 5 µl double stranded cDNA, 27 µl Milli Q water, 25 mM $MgCl_2$, 10×PCR buffer, 50×dNTP's, $AMPLI_{GOLD}$ TAQ Enzyme (Perkin Elmer, AmpliTaq Gold with GeneAmp Kit) 5 µl. The PCR was run on a thermal cycler and using the cycle protocol which follows:

| Cycle Temp. | Time | # of Cycles |
|---|---|---|
| 95° C. | 5 minutes | 1 |
| 95° C. | 30 seconds | 35 |
| 55° C. | 60 seconds | 35 |
| 72° C. | 90 seconds | 35 |
| 72° C. | 10 minutes | 1 |
| 30° C. | 1 minute | 1 |

The amplified cDNA products were run on a 1.5% agarose gel with ethidium bromide for size verification.

Cloning, Transformation and Sequencing

Verified PCR products were gel extracted (GIBCO gel purification kit) and precipitated using Pellet Paint Co-Precipitant kit (Novagen). Once precipitated, cDNA ends were phosphorylated with kinase in preparation for closing. Samples were ligated into the pSMART vector and transformed into *E. cloni* cells (Lucigen) using the Lucigen CloneSmart Blunt Cloning kit. Successfully transformed clones were cultured in Terrific Broth with 50 µl/mL ampicillin for one hour and then plated to allow for overnight growth.

The samples were tested for the correct insert size by PCR and gel electrophoresis. Samples containing the correct insert size were submitted for DNA sequencing.

It may be concluded that ω-ACTX-Hv2a and its variants as described herein are potent and extremely specific antagonist of insect voltage-gated calcium channels. The toxins have no effect on potassium and sodium currents in either bee brain or mouse trigeminal neurons.

Based on the data presented in FIG. 7, ω-ACTX-Hv2a may be calculated as having >50,000-fold preference for insect versus vertebrate calcium channels, making it >25,000-fold more selective than ω-agatoxin-IVA (which only has a 2-fold preference). Thus, ω-ACTX-Hv2a is one of the most invertebrate-selective peptide toxins discovered to date.

Examples 1-6 can be repeated to produce the variants shown in Tables 1-2 and to determine their effectiveness. The variants likewise are most effective insect-selective peptide toxins.

While the invention has been described with respect to certain embodiments, those skilled in the art will readily appreciate that various changes and/or modifications can be made to the invention without departing from the scope of the invention, and such changes and/or modifications are to be included within the spirit and purview of this application and the scope of the appended claims.

We claim:

1. An isolated polypeptide having insecticidal activity comprising a member selected from the group consisting of the mature toxin sequence of polypeptides having the sequences of SEQ ID NO: 2-35, is approximately 36-37 amino acids in length, has a molecular mass of approximately 4,000-5,000 Daltons, and is capable of forming 3 intrachain disulfide bonds and binding with an insect calcium channel.

2. An isolated polypeptide having insecticidal activity derived from funnel web spider *atrax robustus* comprising a member selected from the group consisting of the mature toxin sequence of polypeptides having the sequences of SEQ ID NO: 3, 9, 17, 18, 27 and 28, is approximately 36-37 amino acids in length, has a molecular mass of approximately 4,000-5,000 Daltons, and is capable of forming 3 intrachain disulfide bonds and binding with an insect calcium channel.

3. An insecticide composition comprising an insecticidally effective amount of a polypeptide of claim 1 and an agriculturally acceptable carrier.

4. A method of screening for substances having antagonistic activity with respect to insect voltage-gated calcium channel comprising the steps of: (a) screening a series of compounds to determine those compounds which inhibit the binding of a member selected from the mature toxin sequence of group of SEQ ID NO: 2-35 according to claim 1, to insect calcium channels and (b) testing the ability of such inhibitory compounds to act as an antagonist of insect calcium channels.

5. A method of screening for substances having antagonistic activity with respect to insect voltage-gated calcium channel comprising the steps of: (a) screening a series of compounds to determine those compounds which inhibit the binding of a member selected from the group of the mature toxin sequence of SEQ ID NO: 2-35 according to claim 1, to insect calcium channels; (b) screening those compounds which inhibit the binding of said group member for interaction with insect calcium channels to identify those compounds with a dissociation constant for its interaction with the insect calcium channels of less than about 10-7M, and (c) determining whether any compound identified with a dissociation constant for its interaction with the insect calcium channels has minimal activity against vertebrate calcium channels.

* * * * *